United States Patent [19]
Nakajima et al.

[11] Patent Number: 5,985,213
[45] Date of Patent: *Nov. 16, 1999

[54] SIMPLIFIED ENVIRONMENTAL ATMOSPHERE MEASURING APPARATUS

[75] Inventors: Eiichi Nakajima; Yasuo Udoh; Tsutomu Iikawa; Toshisuke Kitakohji; Teruo Motoyoshi; Takashi Furusawa; Shiori Yamazaki; Masao Nakayama; Michiko Satoh; Shigeru Fukushima; Mayumi Itabashi, all of Kawasaki, Japan

[73] Assignee: Fujitsu Limited, Kawasaki, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/475,502

[22] Filed: Jun. 7, 1995

Related U.S. Application Data

[62] Division of application No. 08/178,357, Jan. 4, 1994, which is a continuation-in-part of application No. 08/140,153, filed as application No. PCT/JP93/00277, Mar. 4, 1993, abandoned.

[30] Foreign Application Priority Data

| Mar. 4, 1992 | [JP] | Japan | 4-46897 |
| Aug. 17, 1992 | [JP] | Japan | 4-217069 |
| Apr. 30, 1993 | [JP] | Japan | 5-104524 |

[51] Int. Cl.$^6$ ................................. G01N 17/04
[52] U.S. Cl. ................. 422/53; 422/61; 422/88
[58] Field of Search ........................ 422/53, 61, 88; 436/178, 181

[56] References Cited

U.S. PATENT DOCUMENTS

| 3,329,004 | 7/1967 | King, Jr. | 73/23 |
| 4,235,098 | 11/1980 | Tisch | 73/28 |
| 4,508,624 | 4/1985 | Nagata | 210/658 |
| 4,759,210 | 7/1988 | Wohltjen | 73/23 |
| 4,869,874 | 9/1989 | Falat | 422/53 |

FOREIGN PATENT DOCUMENTS

| 0 120 203 | 10/1984 | European Pat. Off. . |
| 17 73 968 | 8/1968 | Germany . |
| 21 51 693 | 10/1971 | Germany . |
| 32 09 013 | 10/1983 | Germany . |
| 63-177737 | 11/1988 | Japan . |
| 63-305232 | 12/1988 | Japan . |
| 64-072062 | 3/1989 | Japan . |
| 1-160349 | 11/1989 | Japan . |
| 1-290552 | 11/1989 | Japan . |
| 3-089162 | 4/1991 | Japan . |
| 3-076148 | 7/1991 | Japan . |
| 3-296647 | 12/1991 | Japan . |
| 1 223 132 | 2/1971 | United Kingdom . |
| 1 515 421 | 6/1978 | United Kingdom . |
| 1 527 302 | 10/1978 | United Kingdom . |
| 2 158 816 | 11/1985 | United Kingdom . |

OTHER PUBLICATIONS

*Patent Abstracts of Japan*, vol. 13, No. 138 (P–852) Apr. 6, 1989 & JP–A–63 305232 (Fujitsu Ltd) Dec. 13, 1988.

*Primary Examiner*—Jeffrey Snay
*Attorney, Agent, or Firm*—Staas & Halsey

[57] ABSTRACT

When adsorbed gas is analyzed after metal, ceramics or metallic salt has been left in an environmental atmosphere for a predetermined period of time, an average concentration of specific gas over a long period of time can be accurately measured with an inexpensive small apparatus. Especially, porous metal or ceramics (transition metal oxide) are excellent in selective adsorption properties for $NO_x$, porous ceramics (rare earth element oxide) are excellent in selective adsorption properties for $CO_2$, and a specific chloride such as copper chloride and silver chloride is excellent in selective adsorption properties for $SO_2$. A test kit accommodating such test pieces in a case, a protective case for the test kit to put the test kit into practical use, an umbrella and a forced air blowing unit are also disclosed.

26 Claims, 25 Drawing Sheets

(A)

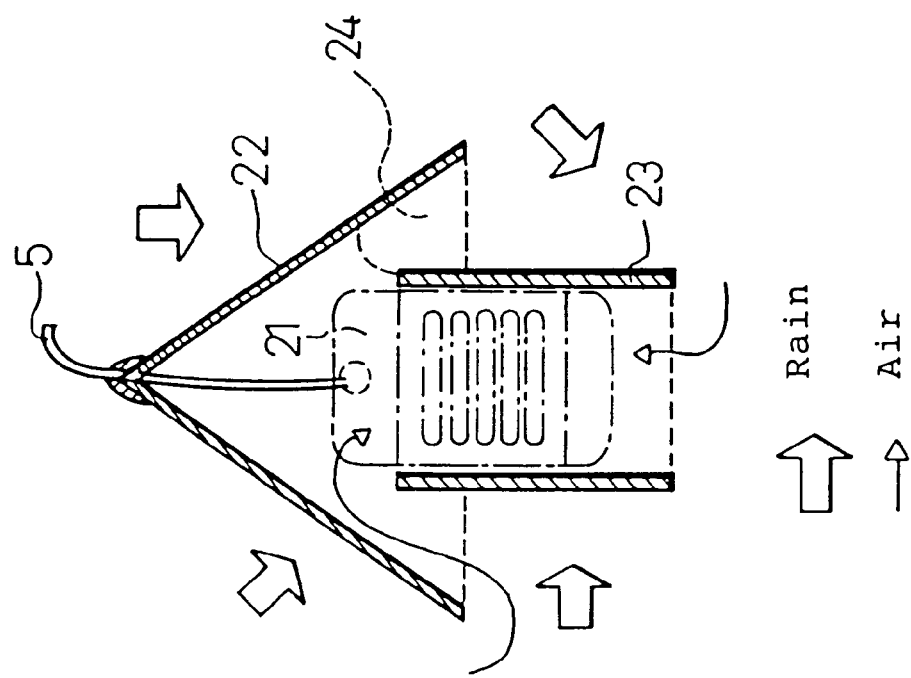
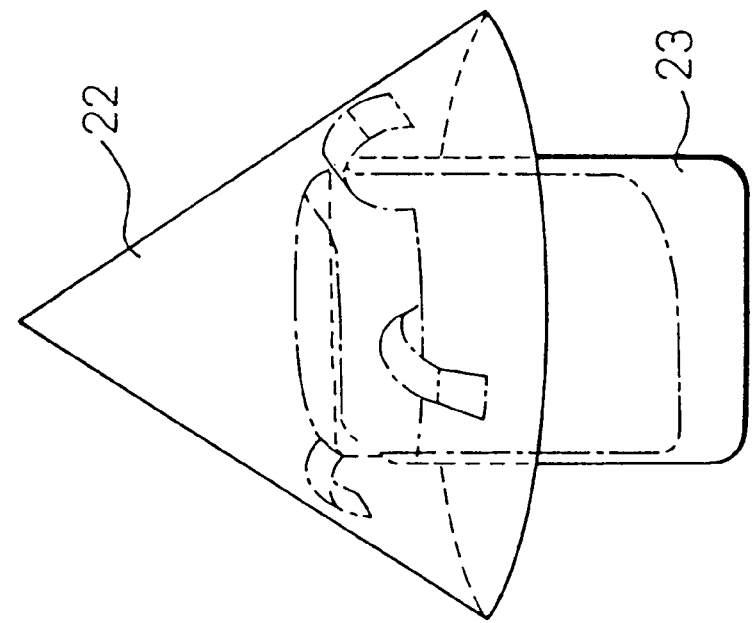

Period of time for which test pieces were left (day)

Fig.25

| Metal \ Group | No color change | I | II | III |
|---|---|---|---|---|
| Copper | | | | |
| Silver | | | | |
| Iron-nickel alloy | | | | |
| Aluminum | | | | |
| Iron | | | | |

IRON-NICKEL ALLOY FOR SO₂

ESTIMATED CONCENTRATION (ppb)

SILVER FOR H₂S

ESTIMATED CONCENTRATION (ppb)

COPPER FOR CHLORINE-CONTAINING GAS

ESTIMATED CONCENTRATION (ppb)

IRON FOR HUMIDITY

ESTIMATED HUMIDITY (%)

SIMPLIFIED ENVIRONMENTAL ATMOSPHERE MEASURING APPARATUS

This application is a division of application Ser. No. 08/178,357, filed Jan. 4, 1994, which is a CIP of parent application Ser. No. 08/140,153, filed Nov. 4, 1993, now abandoned, which is a 37 of PCT JP93/00277, filed Mar. 4, 1993.

TECHNICAL FIELD

The present invention relates to a simplified environmental atmosphere measuring method and apparatus, and more particularly relates to a simplified environmental atmosphere measuring method, a measuring kit and a protective case for test pieces, which is capable of measuring the atmosphere in an environment when simple test pieces are left in the environment to be measured and then collected after a predetermined period of time has passed and then the gas to be tested is measured.

BACKGROUND TECHNIQUE

Recently, $NO_x$, $CO_2$, $SO_2$ and the like existing in the atmosphere have become a serious environmental problem. The cause of $NO_x$ is exhaust gas discharged from automobiles and factories. In the natural world, the concentration of $NO_2$ and NO is several ppb. On the other hand, in big cities, the concentration of $NO_2$ and NO is 50 ppb at the maximum, which causes a serious social problem. The situation is the same in the case of $CO_2$. Further, acid rain causes a serious problem. Air pollution caused by $SO_2$ gas contained in the combustion gas discharged from factories could be one of the factors causing acid rain.

Recently, the size and weight of electronic apparatuses such as electronic computers, for example, personal computers, word processors, facsimiles, telephones, and notebook-type personal computers, tend to be reduced. In these small electronic apparatus, the problem of corrosion occurs. Conventional large-sized electronic computers are installed in air-conditioned environments, so that the problem caused by corrosion rarely occurs. However, small-sized electronic apparatuses are used in all environments. Therefore, not only $H_2S$, Cl and humidity but also $NO_x$, $SO_2$ and the like might affect those electronic apparatus.

The present invention provides a method by which these gases are simply collected and analyzed so that the environment can be monitored.

At present, there is provided a method to monitor the concentration of $NO_x$ for which an expensive large-sized automatic measuring apparatus is used. By the above method, the concentration of $NO_x$ is measured in the following manner: Into a Saltzman reagent in which phosphoric acid, sulfaninilic acid, and Nl naphthyl ethylene diamine hydrochloride are dissolved in distilled water, a predetermined amount of air containing $NO_x$ is sent by an air pump. When this reagent reacts with $NO_x$, the color of the reagent changes to pink. The higher the concentration of $NO_x$ in the reagent is, the denser the color of pink becomes. Next, the reagent is exposed to light, and the concentration of the coloring liquid is measured by a value of the transmission factor.

However, this method is disadvantageous in that: it is not possible to measure the concentration of $NO_x$ at an arbitrary position; and further the period of time to collect data is so short that it is necessary to analyze a large amount of data to know an average concentration over a long period of time. Therefore, this method cannot be applied to many cases.

There is provided a method to monitor the concentration of $CO_2$ for which an expensive large-sized automatic measuring apparatus and a semiconductor sensor are used. It is not possible to apply this measuring method at an arbitrary position. Further, the period of time to collect data is so short that a large amount of data must be analyzed to provide an average concentration over a long period of time. In order to measure the concentration of $CO_2$ gas, a nondispersive infrared analyzer (NDIR) and a gas chromatograph (GC) are commonly used. Into those apparatus, the gas to be measured is introduced, and relative determination is performed in accordance with the absorption rate found from the light absorption coefficient. However, these methods can be applied to only limited locations, that is, in cities, where the measuring apparatus can be easily conveyed and a power source can be easily provided. In a mountainous area, forest or jungle, it is difficult to use these apparatuses.

In order to measure the concentration of $SO_2$ gas, the following method has been known: An absorption solution is put in a collecting bottle, and the bottle is plugged with a cap having a bubbler. When the air in the collecting bottle is sucked by a collecting pump, the environmental air is introduced to the absorption solution, and $SO_2$ gas in the air is trapped by the absorption solution in accordance with the method prescribed by JIS K-0103. After that, the absorption solution is chemically analyzed, and the obtained result is converted into the concentration of gas.

According to the aforementioned method, it is possible to collect only sulfur oxide so that the concentration of sulfur oxide can be accurately provided. However, an operator skilled in operating the entire apparatus is required for normally operating the power source to drive the air pump and for normally operating the collecting device. Therefore, the location and time for sampling are limited.

Further, the following measuring method has been known: After a filter paper has been soaked in a water solution of potassium carbonate, it is air dried. Then, the filter paper is left in an environment so as to collect $SO_2$ gas, which is chemically analyzed and the obtained result is converted into the concentration. According to this alkaline filter paper method, only the filter paper must be set in a location where the environment is measured, so that the gas collecting work is simple. However, $H_2S$ is collected in the form of $SO_3$. Therefore, this method is essentially disadvantageous in that it is impossible to discriminate between $SO_2$ and $H_2S$.

Accordingly, it is desired to provide a method to monitor the average concentrations of $NO_x$, $CO_2$ and $SO_2$ at an arbitrary location over a long period of time.

In order to accomplish the similar object, the present applicant (Fujitsu Co., Ltd.) has developed and disclosed a method in Japanese Unexamined Patent No. Sho. 63-305232, by which the concentration of corrosive gas is monitored with a metallic test piece. However, according to this method, it is difficult to collect $NO_x$ and $CO_2$, and further the obtained result is not accurate. Moreover, it is difficult to discriminate between $SO_2$ and $H_2S$. Therefore, the accuracy cannot be improved.

It is desirable to improve the handling properties of test pieces and also to eliminate the causes to disturb the measuring condition when the test pieces are left in various measuring environments.

It is an object of the present invention to provide a method and means by which the average concentrations of $NO_x$, $CO_2$ and $SO_2$ gases can be simply and accurately monitored in an environmental atmosphere at an arbitrary location with an inexpensive and small-sized apparatus.

DISCLOSURE OF THE INVENTION

In order to accomplish the above object, the present invention is to provide a method for measuring an environment characterized in that: a test piece made of metal, ceramics or metallic salt is set in an environmental atmosphere to be measured; and after a predetermined period of time has passed, $NO_x$, $CO_2$ or $SO_2$ adsorbed by the test piece is subjected to quantitative analysis so as to determine the concentration of $NO_x$, $CO_2$ or $SO_2$ in the environmental atmosphere.

In this specification, it should be understood that the terminology of "adsorption" includes not only physical adsorption but also chemical adsorption in which gas is collected through a chemical reaction.

Specifically, when the concentration of $NO_x$ gas is measured, test pieces made of porous metal or ceramics are used. Alternatively, test pieces made of metal or ceramics, around which metallic particles or ceramic powder is attached, are used. More specifically, it is preferable that the porous or particulate metal is one of copper, silver, platinum, rhodium, ruthenium, palladium, iridium and nickel, and it is also preferable that porous or particulate ceramics is one of $SiO_2$—$Al_2O_3$, $YBa_2Cu_3O_x$, $CrO_2$, $Cr_2O_3$, $Fe_2O_3$, $Co_2O_3$, $SnO_2$, $CoAl_2O_4$, $CuO$, $Al_2O_3$, and $MgO$ (generally, oxide of transition metals). Alternatively, the test piece may be made of porous metal or ceramics, the voids of which are filled with triethanolamine having a function to absorb $NO_x$ gas.

To measure the concentration of $CO_2$ gas, porous rare earth metal oxide is used, for example, a test piece is used which is made of one of $La_2O_3$, $Ce_2O_3$, $Pr_2O_3$, $Nd_2O_3$, $PM_2O_3$, $Sm_2O_3$, $Eu_2O_3$, $Gd_2O_3$, $Tb_2O_3$, $Tb_3O_7$, $Dy_2O_3$, $Ho_2O_3$, $Er_2O_3$, $TM_2O_3$, $Yb_2O_3$, and $Lu_2O_3$.

To measure the concentration of $SO_2$ gas, a chloride of a metal, which metal has a free formation energy of chloride larger than a free formation energy of sulfate, for example, copper chloride or silver chloride is used.

Of course, two or more test pieces may be concurrently used in the monitoring work. Also, the test pieces may be used together with metallic test pieces (copper, silver, aluminum, iron and 52 alloy or some of these) for monitoring corrosive gas as disclosed in Japanese Unexamined Patent No. Sho. 63-305232. Alternatively, the test pieces may be used together with other test pieces (for example, inorganic substance such as platinum, gold and refractory metals) may be used, and further organic substance may be also used.

Also, the present invention is to provide a measuring kit to determine the concentration of $NO_x$, $CO_2$ or $SO_2$ contained in an environmental atmosphere, the measuring kit including: a test piece made of metal, ceramics or metallic salt to selectively adsorb $NO_x$, $CO_2$ or $SO_2$ gas in an environmental atmosphere; and a case used for leaving the test piece in the environmental atmosphere to be measured.

The test piece used for the measuring kit may be a combottleation of the aforementioned test pieces for monitoring $NO_x$, $CO_2$ or $SO_2$ and metallic pieces (or organic substance) disclosed in Japanese Unexamined Patent No. Sho. 63-305232 described before.

According to the present invention, a test piece protective case for environmental investigation is provided so as to be preferably used for the aforementioned measuring kit, the test piece protective case including: a base body to hold a test piece made of metal, ceramics or metallic salt for determining the concentration of an environmental atmosphere; and a cover to cover the test piece, the cover being attached to the base body, wherein a portion of the cover covering a main surface of the test piece or a portion of the base body is transparent so that the main surface of the test piece can be observed from the outside, and an entrance through which the atmospheric gas passes is formed in a portion of the cover or the base body which does not cover the main surface of the test piece.

The use of the test piece protective case for environmental investigation is not limited to a test piece for monitoring $NO_x$, $CO_2$ or $SO_2$ gas, but it can be effectively applied to a test piece protective case for a general environmental investigation.

A preferable embodiment is composed in the following manner: a test piece is placed so that a main surface of the test piece can be located in parallel with a bottom surface of the base body; a cover made of transparent resin is attached to the base body so that the main surface of the test piece can be covered; entrances through which the environmental gas passes are formed on both sides of the main surface of the test piece so that the atmospheric air can flow in parallel with the main surface of the test piece; and a collar is provided for facilitating a flow of the atmospheric air into the atmospheric gas entrance. Further, the preferable embodiment includes an umbrella to shelter the device from rain and snow. Furthermore, the preferable embodiment includes a means to forcibly feed the environmental gas to the main surface of the test piece.

It is preferable that the apparatus is constructed so that the protective case can be used as it is even when the umbrella and the environmental gas feed means are provided. A fan is conveniently used for the environmental gas feed means. When the environmental gas feed means is driven by a solar battery, the power transmission means can be omitted, which is advantageous in the case where the apparatus is used in a remote place.

Further, the present invention provides an umbrella for the test piece protective case, including: a sample fixing portion to accommodate the protective case for the test piece to measure the environmental gas; and an umbrella portion to cover the sample fixing portion for protecting the test piece from rain and snow, wherein the test piece protective case accommodated in the sample fixing portion is provided with an air port through which air passes. A preferable embodiment is constructed in the following manner: the umbrella portion is composed of a conical sheet; the sample fixing portion is composed of a cylindrical portion formed of a sheet, in which a sample is accommodated, and also composed of a plurality of arm portions extending from a top of the conical portion; and the sample fixing portion is attached to the umbrella portion through the arm portions.

Also, the present invention provides a forced-air-blowing unit for the test piece protective case including: an air inlet and an air outlet; a sample accommodating portion and a fan provided in a communicated space between the air inlet and the air outlet, the sample accommodating portion accommodating the protective case for the test piece to measure the environmental gas; and an air flow from the air inlet to the air outlet is caused by the fan. It is preferable that the fan is driven by a battery such as a dry battery or a solar battery.

BRIEF DESCRIPTION OF THE DRAWINGS

FIGS. 4A to 4D are views showing an umbrella for the measuring kit in detail.

FIG. 25 is a color photograph of a table of color samples for detecting gases in an environment:

MOST PREFERRED EMBODIMENT OF THE INVENTION

Monitoring of $NO_x$ gas (1)

Figure 1A:
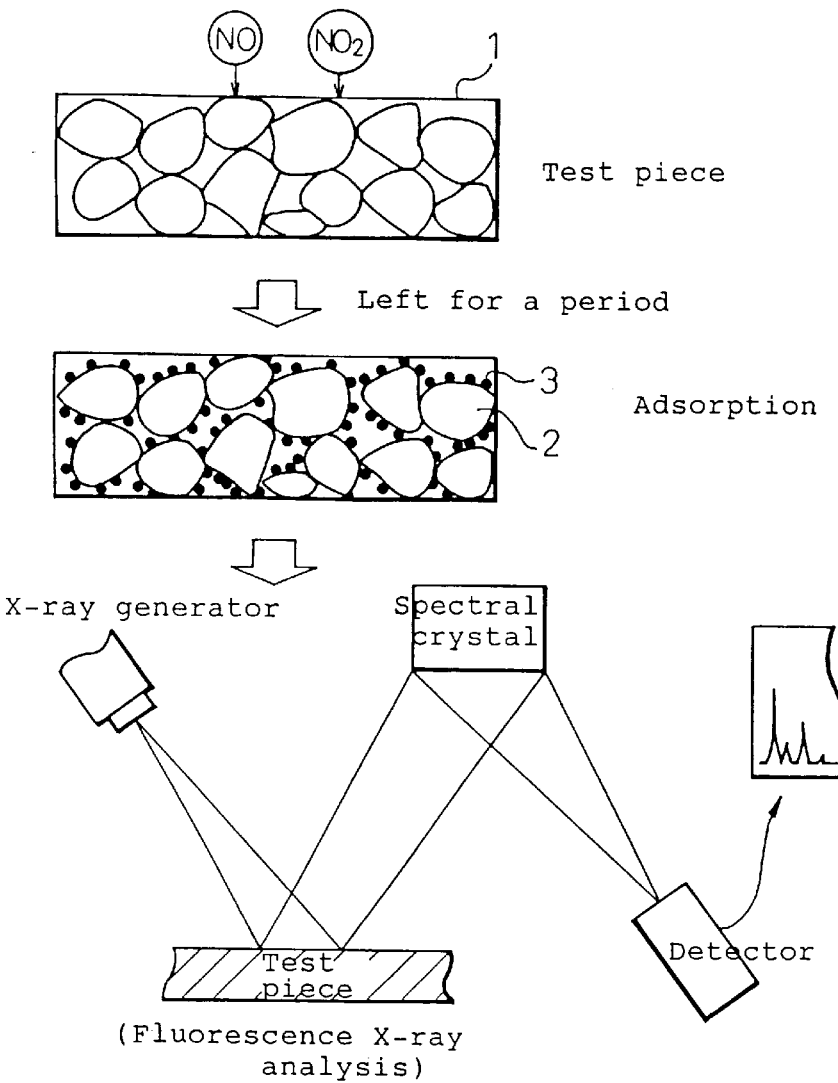
FIG. 1A is a schematic illustration for explaining the principle of the method of the present invention, wherein the explanation is made relating to $NO_x$.

FIG. 1A is a schematic illustration showing the principle of the present invention, relating to the measurement of $NO_x$ gas. According to the present invention, nitrogen oxide in an environment is collected and analyzed in the following manner: A porous metallic or ceramic test piece 1 capable of adsorbing nitrogen oxide is placed in an environment to be measured for a predetermined period of time; nitrogen oxide 3 is adsorbed and collected by the surfaces of the metallic or ceramic particles 2 in the porous structure of the test piece 1; and the adsorbed nitrogen is subjected to quantitative analysis by means of, e.g., fluorescent X-ray spectroscopy so that an amount of the adsorbed nitrogen can be determined. In this case, the nitrogen oxide is only adsorbed by the test piece, or the nitrogen oxide reacts with metal or ceramics of the test piece so as to be fixed. Either will do in the present invention. The environmental atmosphere nitrogen oxide content can be judged according to the result of the analysis.

Figure 1B:
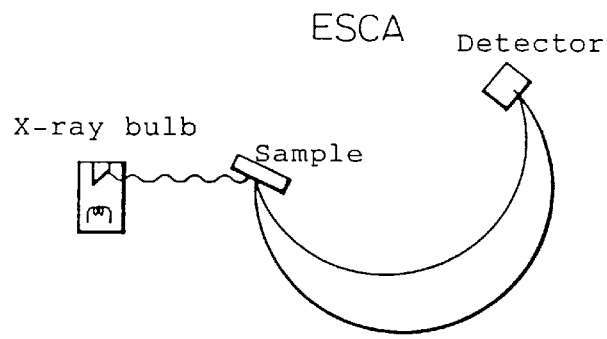
FIG. 1B is a schematic illustration for explaining the quantitative analysis performed by an X-ray electron spectroscopy device (XPS).

The quantitative analysis of nitrogen and the like can be also made with an X-ray electron spectroscopy device (XPS), and the circumstances are shown in FIG. 1B.

Figure 2:
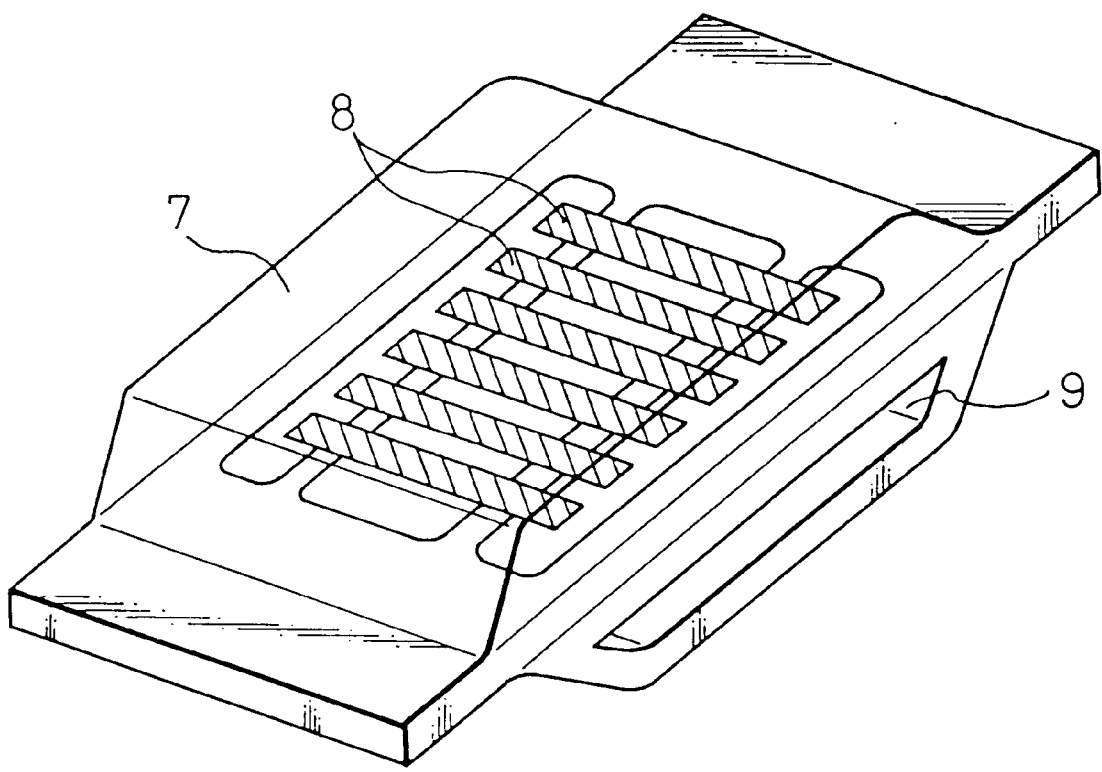
FIG. 2 is a schematic illustration showing the circumstances (measuring kit) in which test pieces of the present invention are accommodated.

FIG. 2 shows an example of the apparatus used for setting the test pieces in an environment. An appropriate number of test pieces 8 are accommodated in a transparent container 7, and an opening 9 is formed on the side of the transparent container 7 so that the outside and inside can be communicated. One of the test pieces 8 is a test piece for measuring nitrogen oxide according to the present invention, and other test pieces are made of metal such as copper, silver and aluminum. These metallic test pieces are used for detecting various substances in an environment (For example, hydrogen sulfide, sodium chloride and moisture are detected.). This container 7 will be described in detail later.

Nitrogen oxide has a relatively low reactivity. Therefore, nitrogen oxide adsorbed onto a surface of simple metal or ceramics is easily scattered, so that the adsorbed amount of nitrogen oxide is not sufficient for measurement.

However, the present inventors employed porous test pieces so as to adsorb nitrogen oxide. They found that the porous test pieces effectively adsorbed a sufficient amount of nitrogen oxide for detection in an environment.

Examples of usable metallic materials to adsorb nitrogen oxide in the present invention are: copper, silver, platinum, rhodium, ruthenium, palladium, iridium and nickel. Preferable ceramic materials are: $SiO_2$—$Al_2O_3$ (especially $SiO_2$-$xAl_2O_3$ ($x \leq 0.15$)), $YBa_2Cu_3O_x$, $CrO_2$, $Cr_2O_3$, $Fe_2O_3$, $Co_2O_3$, $SnO_2$, $CoAl_2O_4$, $CuO$, $Al_2O_3$, and $MgO$.

These materials are excellent in their performance to adsorb and fix nitrogen oxide. Especially when oxide ceramics are in a condition of oxygen deficiency, their fixing capacity for nitrogen oxide is preferably improved. In order to make oxide ceramics oxygen deficient, for example, oxide ceramics may be subjected to heat treatment in a reducing atmosphere.

In order to make porous test pieces, metallic particles or ceramic powder may be simply molded (for example, pressed). Alternatively, metallic particles or ceramic powder may be fired at a relatively low temperature so as to sinter to a porous body of low density.

Alternatively, voids in a piece of porous metal or ceramics may be filled with fine ceramics or metallic powder. For example, fine ceramic powder is attached onto the surface of metallic powder, and this metallic powder is molded or fired to form a porous test piece. In this way, a test piece containing finer ceramics having increased specific areas can be provided as compared with a case in which ceramic particles are simply molded or sintered. Alternatively, a solid metallic or ceramic piece may bear fine ceramic or metallic powder. For example, a solid metallic piece or a metallic sheet may be mechanically processed to form protruded and recessed portions so as to bear ceramic powder. Alternatively, holes or through-holes may be formed in the solid metallic piece or the metallic sheet so as to bear ceramic powder. Alternatively, after a porous sintered metallic or ceramic piece has been made, the sintered piece may be impregnated with fine ceramic or metallic powder.

When triethanolamine $(C_2H_4OH)_3N$ is charged into the voids in a porous metallic or ceramic piece, the same effect can be provided since triethanolamine absorbs nitrogen oxide.

Metallic or ceramic powder to make a test piece is not necessarily limited, however, it is preferable to use powder, the particle size of which is not more than 200 $\mu$m. The reason is as follows. When the particle size is larger than 200 $\mu$m, bonding or necking hardly occurs in the case of sintering performed at low temperature, so that sufficient strength cannot be provided. When the particle size is smaller than 30 $\mu$m, bonding or necking tends to occur even in the case of sintering performed at low temperature, so that there is a possibility that the density is increased and the surface area is lowered. For the reasons described above, in general, it is preferable to use metallic or ceramic powder, the particle size of which is in a range from 30 to 200 $\mu$m. As long as the density of the porous portion of the test piece can be lowered, metallic or ceramic particles, the particle size of which is smaller than 30 $\mu$m, may be used. Powder of small particle size is preferable, because the smaller the particle size is, the more the specific area is increased. In an embodiment to coat, charge or bear the aforementioned fine ceramic powder, very fine ceramic powder, the particle size of which is 0.05 to 5 $\mu$m, may be used.

In the case of porous metal, the density of a test piece is preferably not more than 7 g/cm$^3$, and in the case of porous ceramics, the density of a test piece is preferably not more than 2 g/cm$^3$. In a test piece in which metal and ceramics are compounded, the density is determined in accordance with the compound ratio. When the density is maintained at the values described above, a test piece can be provided, the surface area of which is large, that is, $NO_x$ gas is easily adsorbed to the test piece. Therefore, quantitative analysis can be performed with high sensitivity.

In this connection, the amount of nitrogen oxide adsorbed onto this test piece is determined by the product of gas concentration and time. Therefore, when the test piece is left over a long period of time (for example, for a month) and collected to analyze it with various analyzers, an average gas concentration at the location can be easily determined.

That is, according to the present invention, a small inexpensive and handy monitoring apparatus can be easily provided, thereby an average concentration of $NO_x$ gas can be measured over a long period of time at a location.

Monitoring of $CO_2$ gas

Monitoring the concentration of $CO_2$ gas is performed in the same manner as that of $NO_x$ gas. However, test pieces capable of selectively adsorbing $CO_2$ gas are used. Specifically, a ceramic, made to be porous, and with its density reduced, is used. Especially, porous rare earth metal oxides are used, for example, test pieces are used which are made of one of $La_2O_3$, $Ce_2O_3$, $Pr_2O_3$, $Nd_2O_3$, $Pm_2O_3$, $Sm_2O_3$, $Eu_2O_3$, $Gd_2O_3$, $Tb_2O_3$, $Tb_4O_7$, $Dy_2O_3$, $Ho_2O_3$, $Er_2O_3$, $Tm_2O_3$, $Yb_2O_3$, and $Lu_2O_3$. The inventors have found that $CO_2$ gas in an environment can be effectively adsorbed by the test piece made of the above oxide so as to determine an amount of $CO_2$ gas.

In this case, the porosity, pore size and particle size of the porous test piece can be determined in the same manner as those of the monitoring test piece for $NO_x$ gas.

When an amount of $CO_2$ gas is determined by an X-ray electron spectroscopy device (XPS), a peak for C existing in the range 285 to 290 eV is separated, and a ratio of the surface area of the peak for C corresponding to $CO_2$ based on the surface area of the peaks for C is found. Also, a quantitative value of C is found from the entire area of the C peaks and the peak area of the entire elements to be detected. The product of this quantitative value of C and the area rate corresponds to the quantitative value of $CO_2$.

Monitoring of $SO_2$ gas

Monitoring of $SO_2$ gas is essentially the same as that of $NO_x$. However, test pieces which selectively adsorb and react with $SO_2$ are used. When it is necessary to discriminate between $H_2S$ and $SO_2$, the selectivity of $SO_2$ is important. Therefore, the following investigation was made.

Under the natural condition, the lower the standard formation energy of a substance, the more stably the substance exists. The inventors took notice of this principle, and sought a substance that can be stabilized in the form of sulfate. As a result of the investigation, it has been found that the following sulfates are stable.

| Sulfate | Standard Formation Energy ($\Delta Gf°$/kjmol$^{-1}$) |
|---|---|
| $Ag_2SO_3$ | −411.3 |
| $Ag_2SO_4$ | −618.48 |
| $CuSO_4$ | −660.90 |

Next, a compound of which the standard formation energy is higher than that of the above sulfates may be selected. However, depending on a compound, there is a possibility that the compound reacts with $H_2S$, $NO_2$ and $O_2$ in an environment to generate sulfide, nitrate and oxide. This could be a factor to interrupt the collection of only $SO_2$. Therefore, the standard formation energy of sulfide, nitrate and oxide of copper and silver was investigated. The result of the investigation is shown in following table.

| Sulfide, Oxide, and Nitrate | Standard Formation Energy ($\Delta Gf°$/kjmol$^{-1}$) |
|---|---|
| $Ag_2S$ | −39.46 |
| $Ag_2O$ | −11.21 |
| $AgNO_3$ | −33.47 |
| $Cu_2S$ | −86.20 |
| $CuO$ | −128.12 |
| $Cu(NO_3)_2$ | −102.9 |

As can be seen from the result, a compound of which the standard formation energy is lower than that of sulfide, oxide and nitrate may be selected. Accordingly, the following compounds were selected as the standard formation energy is higher than that of sulfate and lower than that of sulfide, nitrate and oxide.

| Compounds | Standard Formation Energy ($\Delta Gf°/kjmol^{-1}$) |
|---|---|
| AgCl | −109.80 |
| CuCl | −120.9 |

Only a few sulfates and compounds are listed in the above table. Of course, other sulfates and compounds satisfying the aforementioned conditions can be applied.

When test pieces, in which copper chloride CuCl and silver chloride AgCl are used, are prepared in such a manner that the surfaces of copper and silver are chlorinated in an atmosphere of chlorine to form layers of CuCl and AgCl, these test pieces are preferably used from the viewpoints of improvements in handling properties and adhesion properties of CuCl and AgCl layers.

Measuring Kit

The above test pieces, excellent in selective adsorption of $NO_x$, $CO_2$ and $SO_2$, are accommodated in a case and left in an atmosphere to be measured. Therefore, a measuring kit in which at least one test piece is accommodated in the case is usefully applied for measuring $NO_x$, $CO_2$ or $SO_2$ gases in an environment.

As described above, this measuring kit is applied to the test pieces for measuring the concentrations of $NO_x$, $CO_2$ and $SO_2$, and further applied to the metallic test pieces disclosed in Japanese Unexamined Patent No. Sho. 63-305232 and other test pieces (test pieces made of organic substances are included), wherein these test pieces may be accommodated in the measuring kit in combination.

Protective Case (1) In order to accomplish the object of the present invention, the case of the measuring kit accommodates test pieces so that the test pieces can be easily left in an environment to be measured. In the case where a test piece for measuring corrosive gas is accommodated in the case, the corrosive gas comes into contact with the test piece, and then the test piece starts corroding, so that the color of the test piece is changed. Therefore, it is preferable that the change of color can be observed from the outside of the protective case. When an operator's hands carelessly comes into contact with the test piece or water droplets are attached to the test piece, the test piece will be corroded by a factor not relating to the object of measurement. Accordingly it is preferable to protect the test piece with a protective cover of the protective case.

When the test piece is covered in the aforementioned manner, it is necessary to provide an entrance to feed the outside atmosphere onto the surface of the test piece. Therefore, the entrance for the atmosphere is provided in a portion of the cover not covering a main surface of the test piece.

Figure 3A:
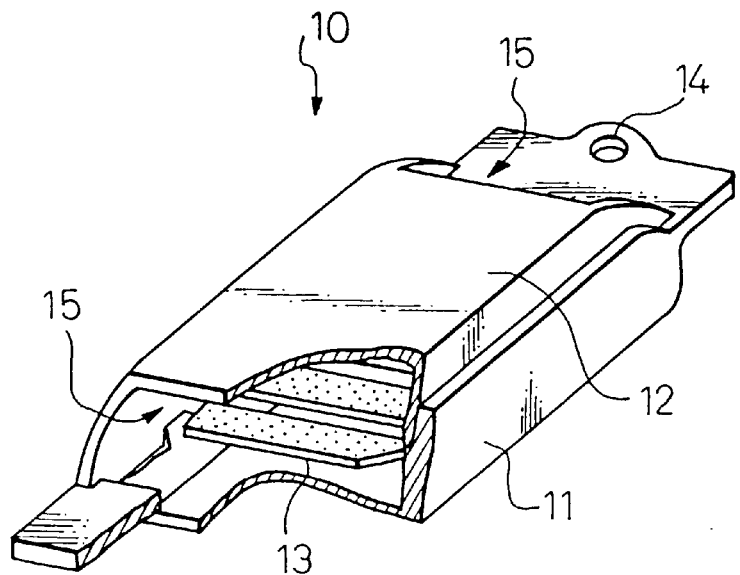
FIGS. 3A to 3E are schematic illustrations showing in detail the same measuring kit as that shown in FIG. 2.
Figures 3B, 3C:
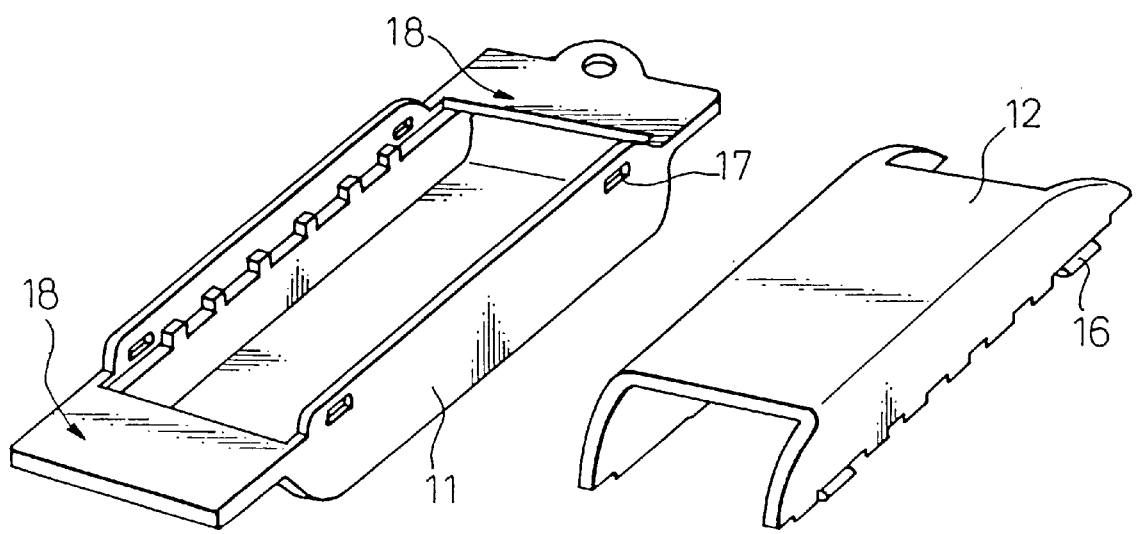
Figure 3D:
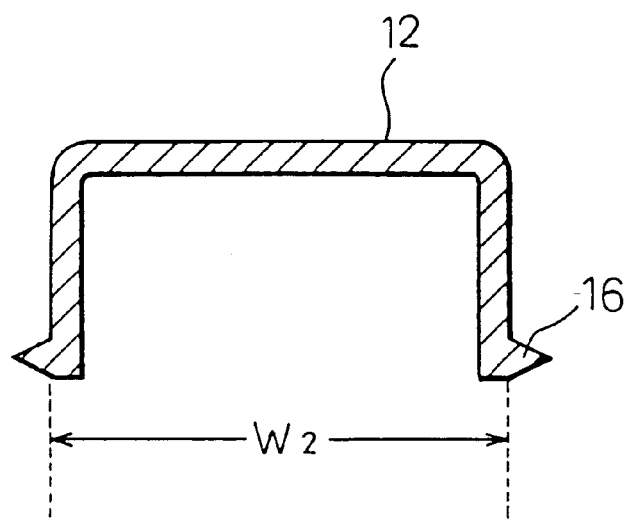
Figure 3E:
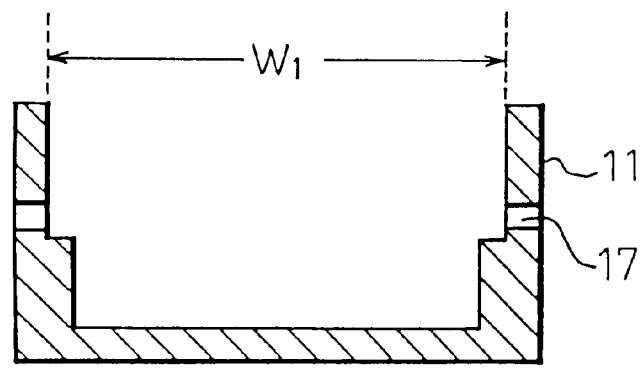

(2) With reference to FIGS. 3A to 3E, a preferable protective case will be explained as follows. FIG. 3B shows a base of the protective case. FIG. 3C shows a cover to be engaged with a base of the protective case. FIG. 3A is a schematic illustration showing a condition in which the cover is engaged with the base. Each of FIGS. 3D and 3E shows a section of the center of the protective case. FIG. 3D shows a cover. FIG. 3E shows the base.

In the drawings, numeral 11 is a side edge of the base, numeral 12 is a cover, numeral 13 is a test piece, numeral 14 is a hole to hang the protective case, numeral 15 denotes air entrances provided on both sides of the protective case, numeral 16 is a protruding portion to fix the cover 12 to the base 11, numeral 17 is a hole to be engaged with the protruding portion 16 of the cover 12, and numeral 18 is a guide to facilitate an air flow to the air entrance 15. The overall length of the protective case is 90 mm, the overall width is 44 mm, and the overall height is 30 mm.

Whereas the surface of the test piece 13 is covered with the cover 12, an operator's hand cannot directly contact the surface of the test piece 13, however, the surface comes into contact with an environmental gas flowing through the air entrances 15.

Both ends of the test piece 13 are supported by side edges 11 of the set base. When the protruding portions 16 of the cover 12 are engaged with the holes 17 on both edges 11, the test piece 13 are fixed in the case. As shown in FIGS. 3D and 3E, the inner width $W_1$ of the set base is designed to be a little smaller than the outer width $W_2$ of the cover 12. Therefore, the cover 12 is preferably fixed to the base by the frictional force generated between the cover 12 and both side edges 11.

The test piece 13 is fixed in parallel with the bottom surface of the set base 11 so that the surface (the main surface) of the test piece 13 can be more contacted with air, and the air entrances 15 are disposed on the right and left sides of the surface of the test piece 13. The air entrances 15 may be provided on either the base 11 or the cover 12 (or on both the base 11 and the cover 12). In general, at least the cover 12 is made of transparent resin, and the air entrances 15 are provided on both the base 11 and the cover 12.

In order to take in outside air as much as possible, the air entrances 15 are preferably provided with guide (reflection plate: guide) 18.

Whereas the upper side of the main surface of the test piece 13 is covered with the cover 12 as described above, water droplets can be prevented from dropping on the test piece 13. When this protective case is hung from an eave, measurements can be performed outdoors. Especially when the protective case is hung through the hole 14 formed on the protective case, the main surface of the test piece 13 is approximately set in a vertical direction, so that the test piece can be protected from rain. When this hole 14 is used, the protective case can be easily hung even indoors.

This protective case can be preferably made by means of injection molding of transparent AS (acrylic styrene). In this case, polycarbonate resin can be also applied.

(3) Even the protective case shown in FIG. 3A can be used outdoors when it is hung from an eaves. When an environmental atmosphere is measured outside of a building which has no eaves (or which has a small eaves) or in an open space without buildings such as a dry river bed, or when the protective case is left under an eaves in the condition of a strong wind, the test piece gets wet in the rain.

In order to solve the above problems, an umbrella is attached to the protective case.

Figure 4C:
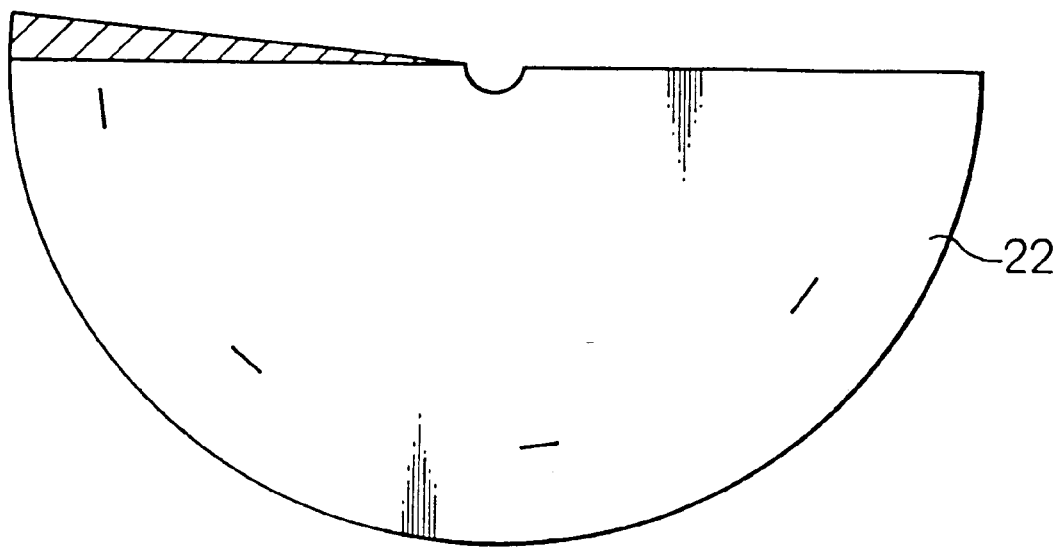
Figure 4D:
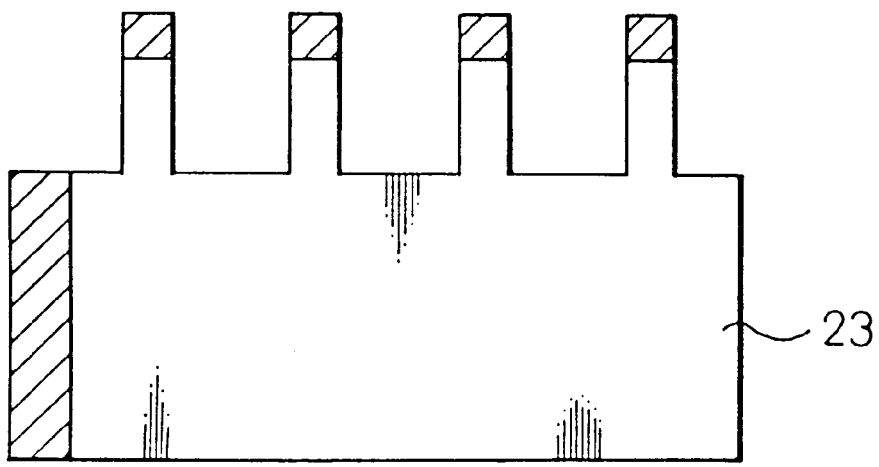

Referring to FIGS. 4A to 4D, FIG. 4A is a perspective view of the protective case (measuring kit) having an umbrella, FIG. 4B is a longitudinal sectional view of the protective case having an umbrella, and FIGS. 4C and 4D are development views showing the structure of the umbrella.

This umbrella is made of film-like organic material or sheet-like metallic material. An umbrella portion 22 shown in FIG. 4C covers an upper portion of a sample 21 for measuring an environment. A ventilation hole 24 formed between the sample 21 and the umbrella portion 22 is maintained at a position higher than the edge of the umbrella portion 21. In the aforementioned manner, a sample fixing portion 23 shown in FIG. 4D is combined with the umbrella portion 22 as shown in FIG. 4A. The umbrella portions 21 and the sample fixing portion 23 are assembled in the aforementioned manner.

In this case, the sample 21 can be the protective case (measuring kit) itself shown in FIG. 3A, and this sample 21 is fixed to the sample fixing portion 23 by some means. The fixation can be performed by means of a cord, frictional force, hook and the like.

When this umbrella is used as shown in FIGS. 4A and 4B, an upper portion of the sample 21 does not get wet in the rain being covered with the umbrella portion 22 disposed above the sample 21, and a side portion of the sample 21 does not get wet with the rain being covered with the sample fixing portion 23 disposed on the side of the sample. However, the air to be investigated can be ventilated by the air entrance 24 provided between the sample and the umbrella. Therefore, the air is sufficiently comes into contact with the sample. Whereas this air entrance is located at a position higher than the skirt of the umbrella, rain does not enter the air entrance.

Whereas the umbrellas of this type are made of sheet-shaped material, they can be mass-produced at low cost. Further, the produced umbrellas can be easily stored. Furthermore, they can be easily assembled, and the samples can be easily attached to them. Therefore, the conventional samples can be applied to the umbrellas as they are. The sample and umbrella can be simply hung with a cord. However, since the skirt of the sample fixing portion is horizontal, the sample and umbrella may be placed at a location where there is no rain water.

When at least a portion of the umbrella is made of transparent material, the color change of the sample can be observed at any time.

(4) In order to measure the average gas concentration over a long period of time, test pieces are left in an environment for a predetermined period of time, and then they are observed and analyzed. In some cases, it is desired to reduce the period of time in which the test pieces are left in the environment. In order to accomplish the above object, the atmospheric air is forcibly sent to the test pieces so as to facilitate the reaction between the environmental gas and the test pieces.

Therefore, the inventors have devised an apparatus by which fresh air can be blown against the surface of a test piece when the protective case (measuring kit) shown in FIG. 3A is attached to the apparatus. In this case, air is blown by a fan. Alternatively, air may be sent to the test piece when a convection is generated by heated air. From the viewpoint of safety and simplicity, the fan is advantageously used.

Figure 5A:
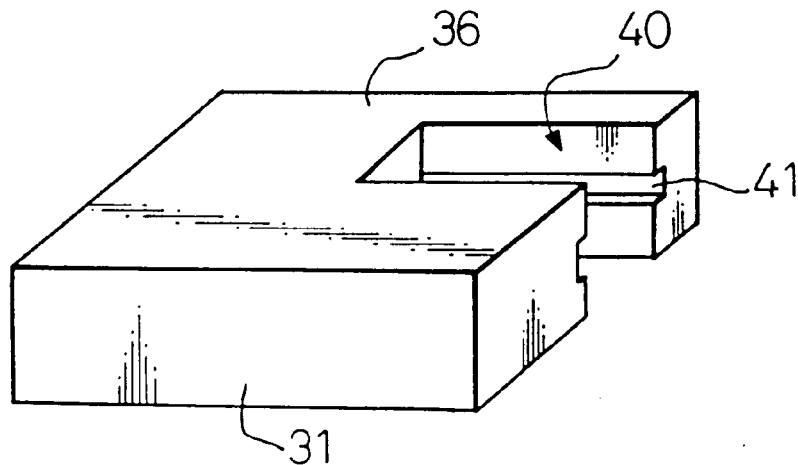
FIGS. 5A and 5B, FIGS. 6A and 6B, FIGS. 7A to 7C are respectively schematic illustrations showing various embodiments of the acceleration test device to be combined with the measuring kit.
Figure 5B:
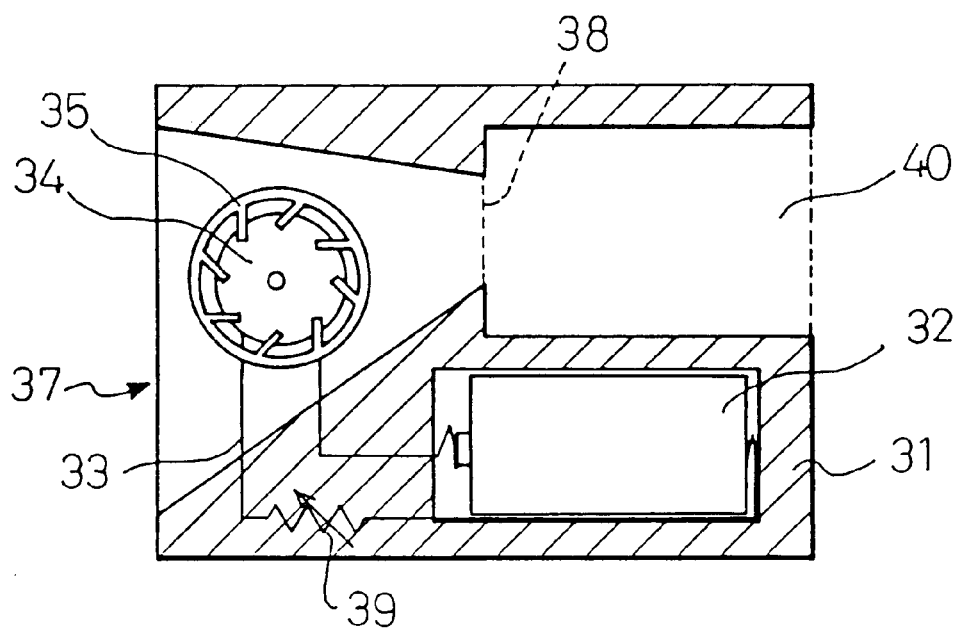

FIGS. 5A and 5B show the first embodiment. This embodiment is constructed in the following manner: air is taken in from one side of the apparatus; the used air is discharged from the other side; and a test piece is disposed between the two sides.

FIG. 5A is a perspective view showing the outer appearance, and FIG. 5B is a sectional view showing the horizontal section of the apparatus as a model.

A dry battery 32 is attached to a measurement accelerating device 31. In this case, a solar battery may be used for the purpose of preventing the consumption of the dry battery. Alternatively, an alternating current power source may be used. Then a motor 34 connected with the battery 32 through a lead wire 33 is driven, and a fan 35 is rotated. When an upper cover 36 is set, the air taken in from an air entrance 37 is moved to an air outlet (referred to as an outlet hereinafter) 38, so that the air is blown out from the outlet 38 at a constant speed. The air speed can be adjusted when the speed of rotation of the motor 34 is changed. The speed of rotation of the motor 34 can be changed by a variable resistor 39 connected with the lead wire in series.

The protective case 10 shown in FIG. 3A in which the test piece 13 is set, is attached to a case setting portion 40. The test piece is not directly set in the apparatus, but the protective case 10 is set, in which the test piece 13 is set as described above, which is effective in that: the test piece can be easily handled; and the corrosion of the test piece caused when an operator's hand carelessly comes into contact with the test piece surface can be prevented. Whereas the case 10 is attached along a groove 41 formed in the case setting portion 40, it can be horizontally fixed with respect to the measurement-acceleration device 31, so that the air flow can be maintained in parallel with the surface of the test piece.

The air blown out from the outlet 38 enters the attached case 10 through one of the air entrances 15 of the attached case 10, and comes into contact with the surface of the test piece 13. After that, the air is discharged from the other air entrance 15.

The test piece 13 reacts with gases contained in the introduced air, and a reaction peculiar to the combination of the test piece and the gases is caused.

Materials used for the acceleration device body 31, upper cover 36 and fan 35 are selected from the organic materials such as acrylic resin, polycarbonate resin and polystyrene that cannot be corroded by gas.

The dry battery 32, lead wire 33, motor 34 and variable resistor 39 are protected by measurement-acceleration device body 31 so that they cannot be corroded by gas.

Figure 6A:
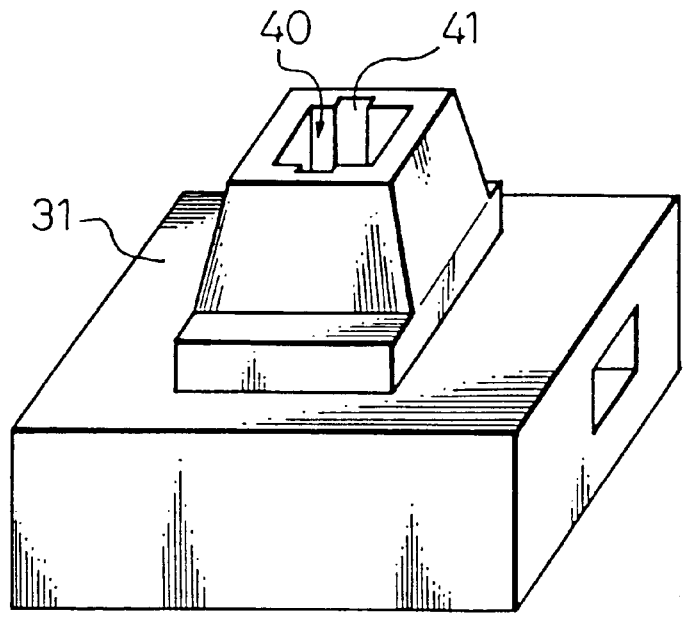
Figure 6B:
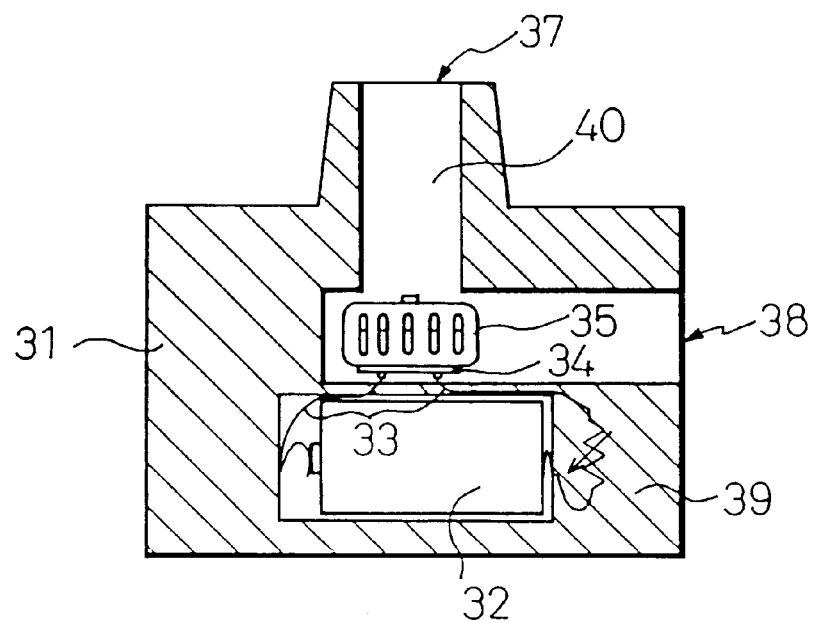

FIGS. 6A and 6B show the second embodiment in which air is vertically taken in from an upper position and horizontally discharged, or air is horizontally taken in and vertically discharged. FIG. 6A is a perspective view showing the appearance, and FIG. 6B is a longitudinal sectional view. Like parts in each of FIGS. 5A, 5B, 6A and 6B are identified by the same reference character.

The case 10 shown in FIG. 3A is vertically set in the case setting portion 40 on the top of the apparatus.

Figure 7A:
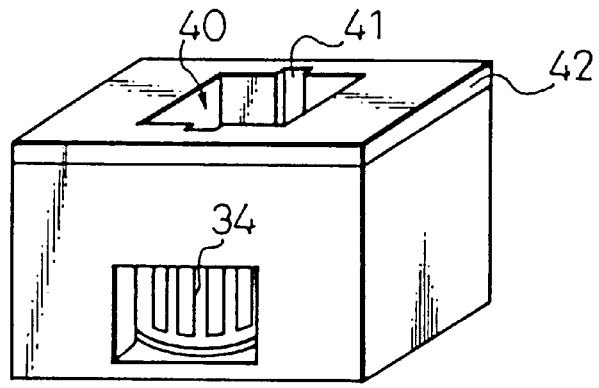
Figure 7B:
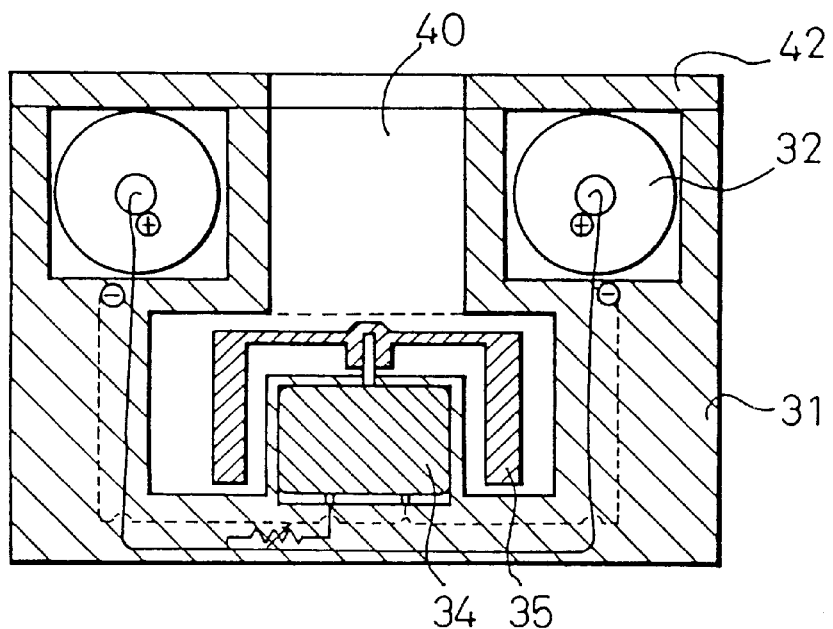
Figure 7C:
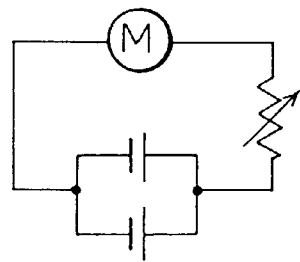

An apparatus shown in FIGS. 7A, 7B and 7C is a variation of the apparatus shown in FIGS. 6A and 6B, and the battery 32 is disposed above the motor 34 and fan 35 so that the battery can be easily replaced when the cover 42 is opened, and further the weight and size of the apparatus are reduced, and furthermore the batteries are connected in parallel so that the consumption of the batteries can be decreased.

FIG. 7A is a perspective view showing the appearance, FIG. 7B is a longitudinal sectional view, and FIG. 7C is an electrical circuit diagram.

EXAMPLES

Example 1

Figure 8A:
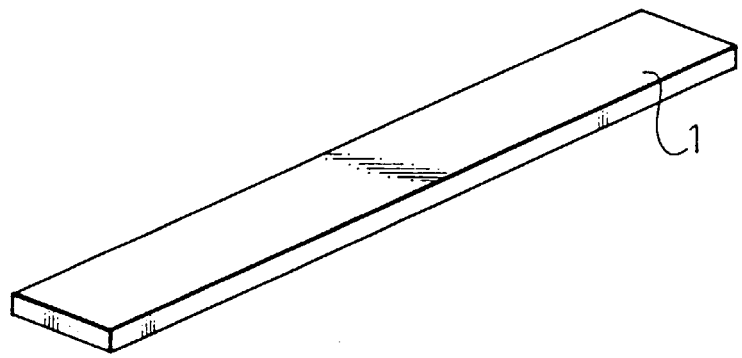
FIGS. 8A to 8C are schematic illustrations showing an $NO_x$ measuring test piece and its inside.
Figure 8B:
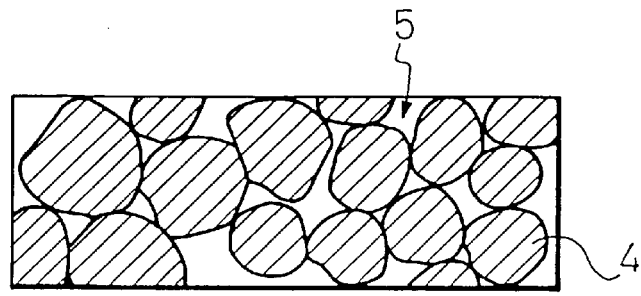
Figure 8C:
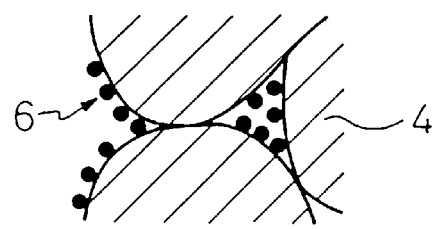

As shown in FIGS. 8A to 8C, porous test pieces of silver Ag and copper Cu were made.

These test pieces 1 were formed into the size of 40 mm×5 mm×1 mm thickness from powder, the particle size of which was 50 µm, by means of press-forming. Next, these test pieces were sintered in a furnace, the atmosphere of which was substituted by hydrogen, at 500° C. for 2 hours, and porous sintered bodies, the densities of which were respectively 6.5 g/cm³ and 6.8 g/cm³, were provided. In FIGS. 8B and 8C, numeral 4 denotes copper particles, numeral 5 denotes voids, and numeral 6 denotes adsorbed $NO_x$ gas.

In order to investigate the effect of collection of $NO_2$ gas, these test pieces were left in a desiccator into which $NO_2$ gas was introduced at a concentration of 10 ppm, for 24 hours.

In order to make certain that the left test pieces had collected gas, they were analyzed with an infrared ray spectral analyzer and a fluorescence X-ray analyzer.

Figure 9:
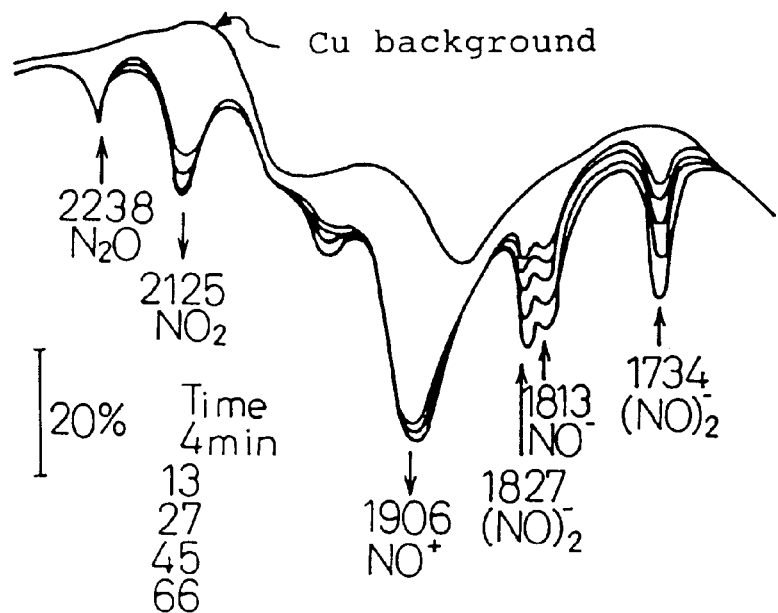
FIG. 9 is an infrared ray spectral diagram in which $NO_x$ adsorbed to a porous copper test piece is analyzed.

An IR spectrum is shown in FIG. 9 in the case where the test pieces were analyzed by means of infrared ray spectral analysis. As can be seen in the drawing, the known absorption wave-number of $NO_x$ corresponds to the wave-number obtained in this analysis. Therefore, it can be made certain that the present test piece absorbed $NO_x$ gas.

Figure 10:
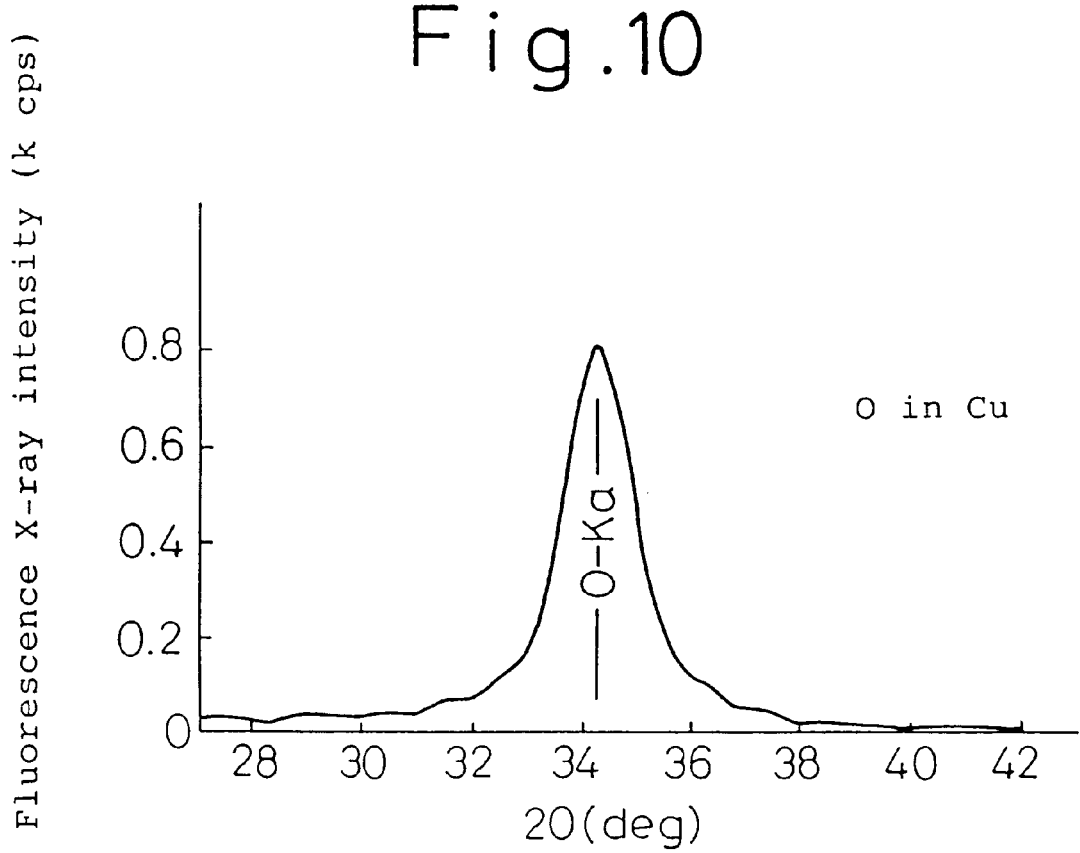
FIGS. 10 and 11 are diagrams showing the X-ray intensity of oxygen (O) and nitrogen (N) contained in a copper test piece measured by fluorescence X-ray analysis.
Figure 11:
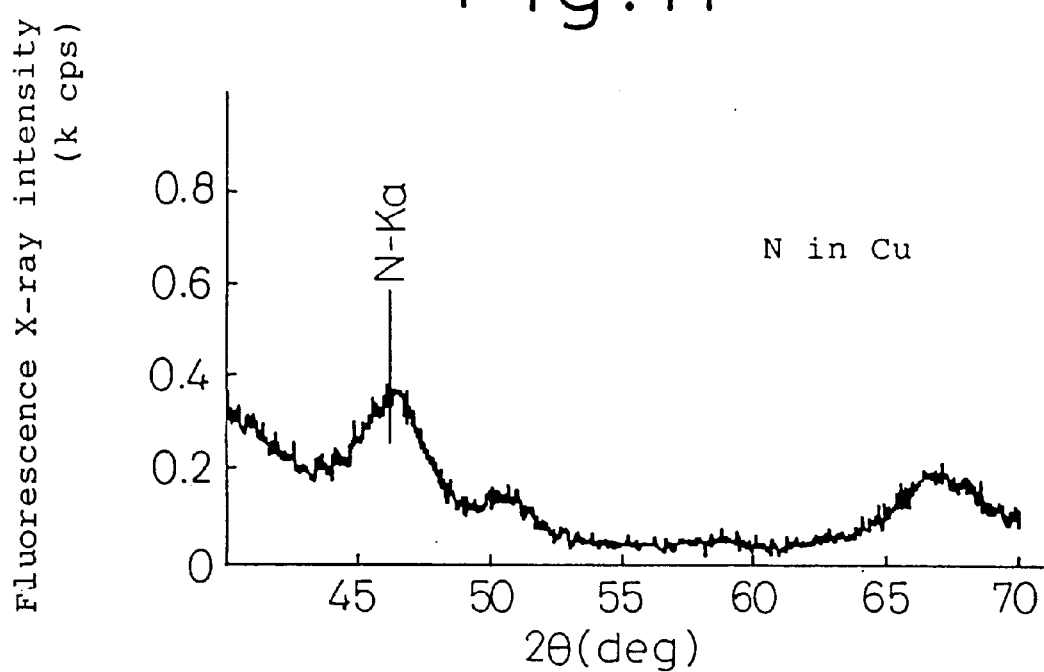

FIGS. 10 and 11 show the result of an analysis in which nitrogen and oxygen of the test pieces were analyzed with the fluorescence X-ray analyzer. FIG. 10 shows the X-ray intensity of oxygen contained in the Cu test piece provided in the fluorescence X-ray analysis. FIG. 11 shows the X-ray intensity of nitrogen contained in the Cu test piece provided in the fluorescence X-ray analysis. From the results of the analysis, it can be understood that oxygen and nitrogen are trapped in both test pieces.

Figure 12:
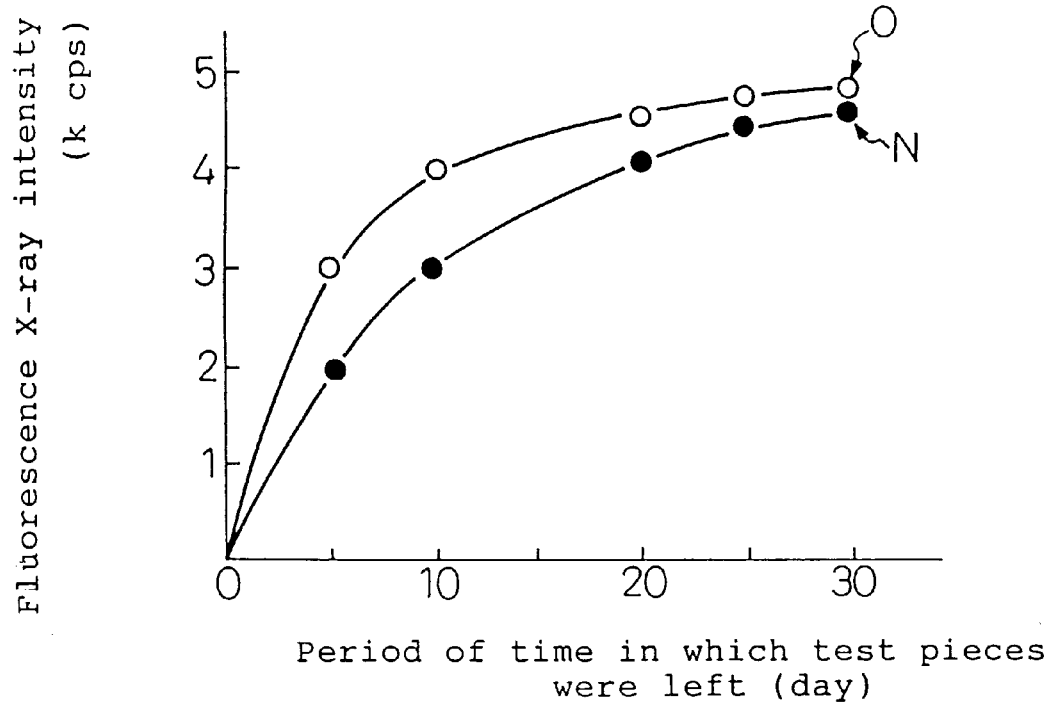
FIG. 12 is a diagram showing a relation between a period of time in which a copper test piece is left in $NO_x$ gas, and fluorescence X-ray intensity of adsorbed oxygen (O) and nitrogen (N).

As a test to put these test pieces into practical use, the present test pieces were left for one month in a desiccator into which $NO_2$ gas was introduced, the concentration of which was 10 ppb. While the test pieces were left, they were taken out from the desiccator every five days, and the X-ray intensity of nitrogen and that of oxygen were measured with the fluorescence X-ray analyzer. As a result of the measurement, as shown in FIG. 12, $NO_2$ gas was not detected in the first stage since the trap amount was small. However, the amounts of nitrogen and oxygen increased until 25 days had passed from the start of measurement, and a sufficient amount for analysis was trapped.

Example 2

In the same manner as that of Example 1, porous ceramic test pieces were made of $SiO_2$-$xAl_2O_3$ (x=0.15) and $YBa_2Cu_3Oy$. These test pieces were formed into the size of 40 mm×5 mm×1 mm thickness from powder, the particle size of which was 50 μm, by means of press-forming. Next, these test pieces were sintered in a furnace, the atmosphere of which was substituted with hydrogen, at 1000° C. for 2 hours, and porous sintered bodies, the densities of which were respectively 1.8 g/cm³ and 2.0 g/cm³, were provided.

In order to investigate the effect of collection of $NO_2$ gas, these test pieces were left in a desiccator into which $NO_2$ gas was introduced at a concentration of 10 ppm, for 24 hours.

In order to make certain that the left test pieces had collected gas, they were analyzed with the infrared ray spectral analyzer and the fluorescence X-ray analyzer.

The same result as that shown in FIG. 9 was provided in the case where the test pieces were analyzed by means of infrared ray spectral analysis. As can be seen in the drawing, the known absorption wave-number corresponds to the wave-number obtained in this analysis. Therefore, it can be made certain that the present test piece had absorbed $NO_x$ gas.

The results of analysis of oxygen and nitrogen are the same as those shown in FIGS. 10 and 11, and it can be understood that oxygen and nitrogen are trapped in both test pieces.

As a test to put these test pieces into practical use, the present test pieces were left for one month in a desiccator into which $NO_2$ gas was introduced, the concentration of which was 10 ppb. In the same manner as that of Example 1, the X-ray intensity of nitrogen and that of oxygen were measured with the fluorescence X-ray analyzer. As a result of the measurement, the same result as shown in FIG. 12 was provided, and $NO_2$ gas was not detected in the first stage since the trap amount was small. However, the amounts of nitrogen and oxygen increased until 25 days had passed from the start of measurement, and sufficient amounts for analysis were trapped.

Example 3

First, copper powder, the particle size of which was 100 μm, and $SiO_2$-$xAl_2O_3$ (x=0.15), the particle size of which was 1 μm, was kneaded by a ball mill, so that fine powder of $SiO_2$-$xAl_2O_3$ was attached onto the surfaces of the copper particles. The copper powder was formed into the size of 40 mm×5 mm×1 mm thickness by means of press-forming. Next, the test piece was sintered in a furnace, the atmosphere of which was substituted with hydrogen, at 500° C. for 2 hours, and the test pieces made of porous sintered bodies, the density of which was 4.0 g/cm³, were provided.

Figure 13:
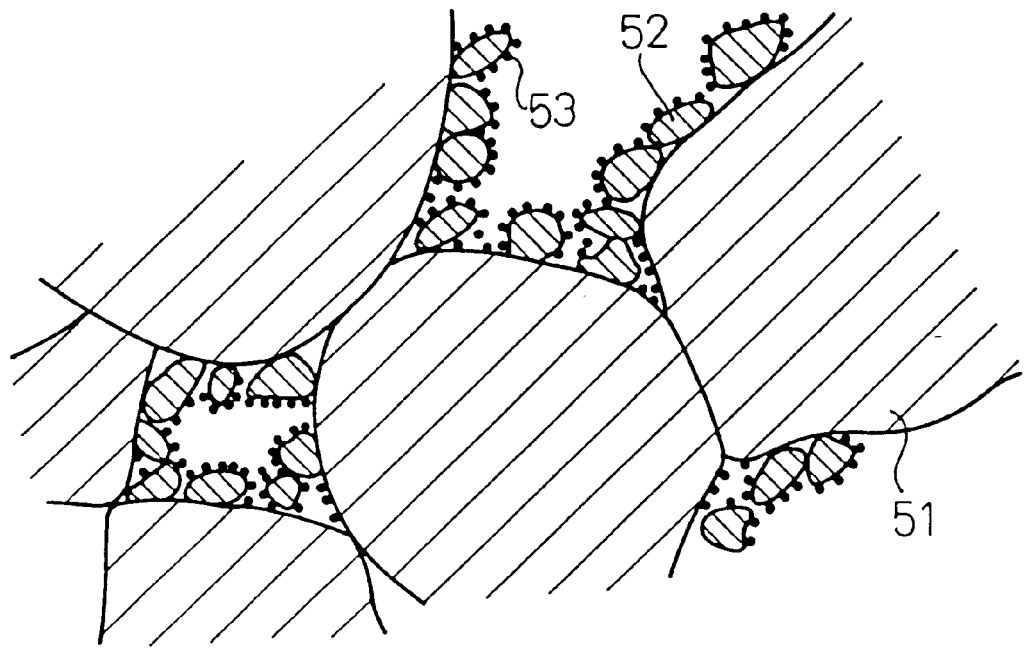
FIG. 13 is a schematic illustration showing the internal structure of a test piece made when copper particles and fine ceramics powders were kneaded and fired.

The inner structure of this test piece is shown in FIG. 13. Numeral 51 denotes copper particles, numeral 52 denotes ceramic particles, and numeral 53 denotes adsorbed nitrogen oxide.

The obtained test piece was left for 24 hours in a desiccator into which $NO_2$ gas was introduced at a concentration of 10 ppm. The left test piece was analyzed with the infrared ray spectral analyzer and the fluorescence X-ray analyzer. Both results provided by the infrared ray spectral analyzer and the fluorescence X-ray analyzer were the same as those of Example 1.

As a test to put these test pieces into practical use, the present test pieces were left for one month in a desiccator into which $NO_2$ gas was introduced at a concentration of which was 10 ppb. In the same manner as that of Example 1, the X-ray intensity of nitrogen and that of oxygen were measured with the fluorescence X-ray analyzer. As a result of the measurement, $NO_2$ gas was not detected in the first stage since the trap amount was small. However, the amounts of nitrogen and oxygen increased until 25 days had passed from the start of measurement, and sufficient amounts for analysis were trapped.

Example 4

Figure 14:
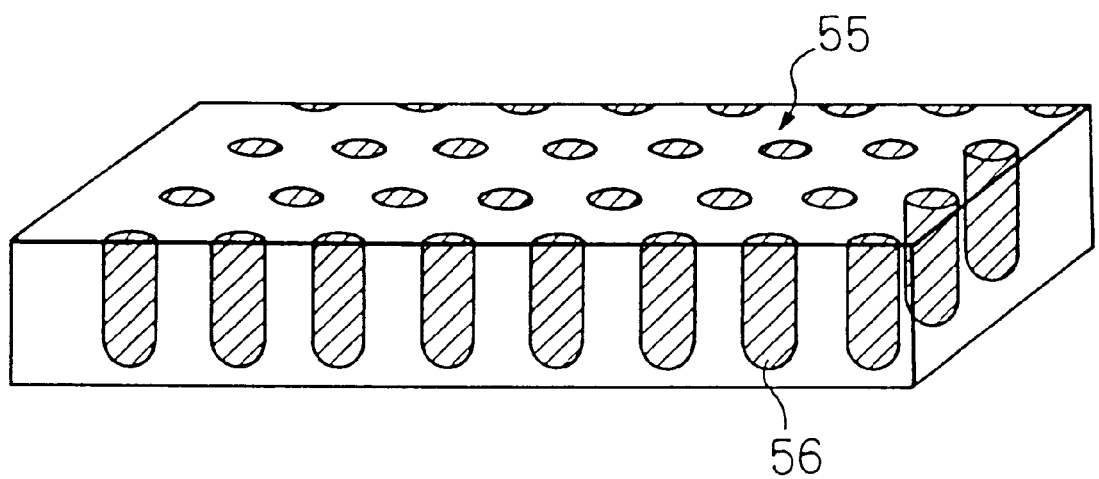
FIG. 14 is a schematic illustration of a test piece made when a large number of holes are formed in a copper piece.

As shown in FIG. 14, a copper piece having a large number of holes was made by means of press-forming. The dimensions of the copper piece was 40 mm×5 mm×1 mm thickness, and the diameter of the holes was 1 mm, and the hole formation density was 25 holes/cm². Fine powder of $SiO_2$-$xAl_2O_3$ (particle size: 10μ) was charged into these holes.

Charging of the powder was performed in the following manner:

Powder of $SiO_2.Al_2O_3$ was previously scattered over the test piece having holes so that the powder was put into the holes. Then, residual powder was removed from the test piece surface. Next, for the purpose of fixing the powder, the test piece was fired at 500° C. in a hydrogen atmosphere for 2 hours. In FIG. 14, numeral 55 is a copper piece, and numeral 56 is a fine ceramic particle charged into the hole of the copper piece.

The present test piece was left for 24 hours in a desiccator into which $NO_2$ was introduced at a concentration of 10 ppm. The left test piece was analyzed with the infrared spectral analyzer and the fluorescence X-ray analyzer. As a test to put the test piece into practical use, the present test piece was left for one month in a desiccator into which $NO_2$ gas was introduced at a concentration of 10 ppb. The X-ray intensity of nitrogen and that of oxygen were measured with the fluorescence X-ray analyzer.

The same result as that of Example 1 was provided.

Example 5

First, $SiO_2$-$xAl_2O_3$ of which the particle size was 100 μm and Cu powder of which the particle size was 1 μm were kneaded with a ball mill so that Cu powder was attached onto the surfaces of the particles of $SiO_2$-$XAl_2O_3$. This ceramic powder was formed into a piece of which the size was 40 mm×5 mm×1 mm thickness, then the piece was sintered at 1000° C. for 2 hours in a furnace of which the atmospheric gas was substituted by hydrogen, so that a test piece made of a sintered body of which the density was 2.4 $g/cm^2$ was provided.

The present test piece was left for 24 hours in a desiccator into which $NO_2$ gas was introduced at a concentration of 10 ppm. The left test piece was analyzed with the infrared spectral analyzer and the fluorescence X-ray analyzer. As a test to put the test piece into practical use, the present test piece was left for one month in a desiccator into which $NO_2$ gas was introduced at a concentration of 10 ppb. The X-ray intensity of nitrogen and that of oxygen were measured with the fluorescence X-ray analyzer.

The same result as that of Example 1 was provided.

Example 6

As shown in FIG. 14, a ceramic piece having a large number of holes was made by means of press-forming. The dimensions of the ceramic piece was 40 mm×5 mm×1 mm thickness, and the diameter of the holes was 1 mmφ, and the hole formation density was 25 holes/$cm^2$. Fine powder of Cu was scattered over the test piece having holes so that the powder was put into the holes. Then, residual powder was removed from the test piece surface. Next, for the purpose of fixing the powder, the test piece was fired in a furnace with a hydrogen atmosphere for 2 hours at 500° C. In FIG. 14, numeral 55 is a ceramic piece, and numeral 56 is Cu powder charged into the holes in the ceramic piece.

The present test piece was left for 24 hours in a desiccator into which $NO_2$ was introduced at a concentration of 10 ppm. The left test piece was analyzed with the infrared spectral analyzer and the fluorescence X-ray analyzer. As a test to put the test piece into practical use, the present test piece was left for one month in a desiccator into which $NO_2$ gas was introduced at a concentration of 10 ppb. The X-ray intensity of nitrogen and that of oxygen were measured with the fluorescence X-ray analyzer.

The same result as that of Example 1 was provided.

Example 7

In the same manner as that shown in Example 1, a porous test piece of Cu was made. This test piece was made of Cu powder of which the particle size was 50 μm, and formed into a piece of 40 mm×5 mm×1 mm thickness by means of press-forming. Next, this piece was sintered at 500° C. for 2 hours in a furnace, the atmospheric gas of which was substituted by hydrogen, so that a porous sintered body of which the density was 6.8 $g/cm^3$ was provided. Next, this copper piece was dipped in triethanolamine for 24 hours, so that the copper piece was sufficiently permeated with triethanolamine.

The present test piece was left for 24 hours in a desiccator into which $NO_2$ was introduced at a concentration of 10 ppm. The test piece was analyzed with the infrared spectral analyzer and the fluorescence X-ray analyzer. As a test to put the test piece into practical use, the present test piece was left for one month in a desiccator into which $NO_2$ gas was introduced at a concentration of 10 ppb. The x-ray intensity of nitrogen and that of oxygen were measured with the fluorescence X-ray analyzer.

The same result as that of Example 1 was provided.

Example 8

As shown in FIGS. 8A to 8C, a porous test piece of $Tb_2O_3$ was made. This test piece was made of powder of which the particle size was 50 μm, and formed into a piece of 40 mm×5 mm×1 mm thickness by means of press-forming. Next, this piece was sintered at 500° C. for 2 hours in a furnace, the atmospheric gas of which was substituted by hydrogen, so that a porous sintered body of which the density was 2.7 $g/cm^3$ was provided.

In order to investigate the effect of collection of $CO_2$ gas, the test piece was left in a desiccator into which $CO_2$ gas was introduced at a concentration of 10 ppm, for 100 hours.

Figure 15:
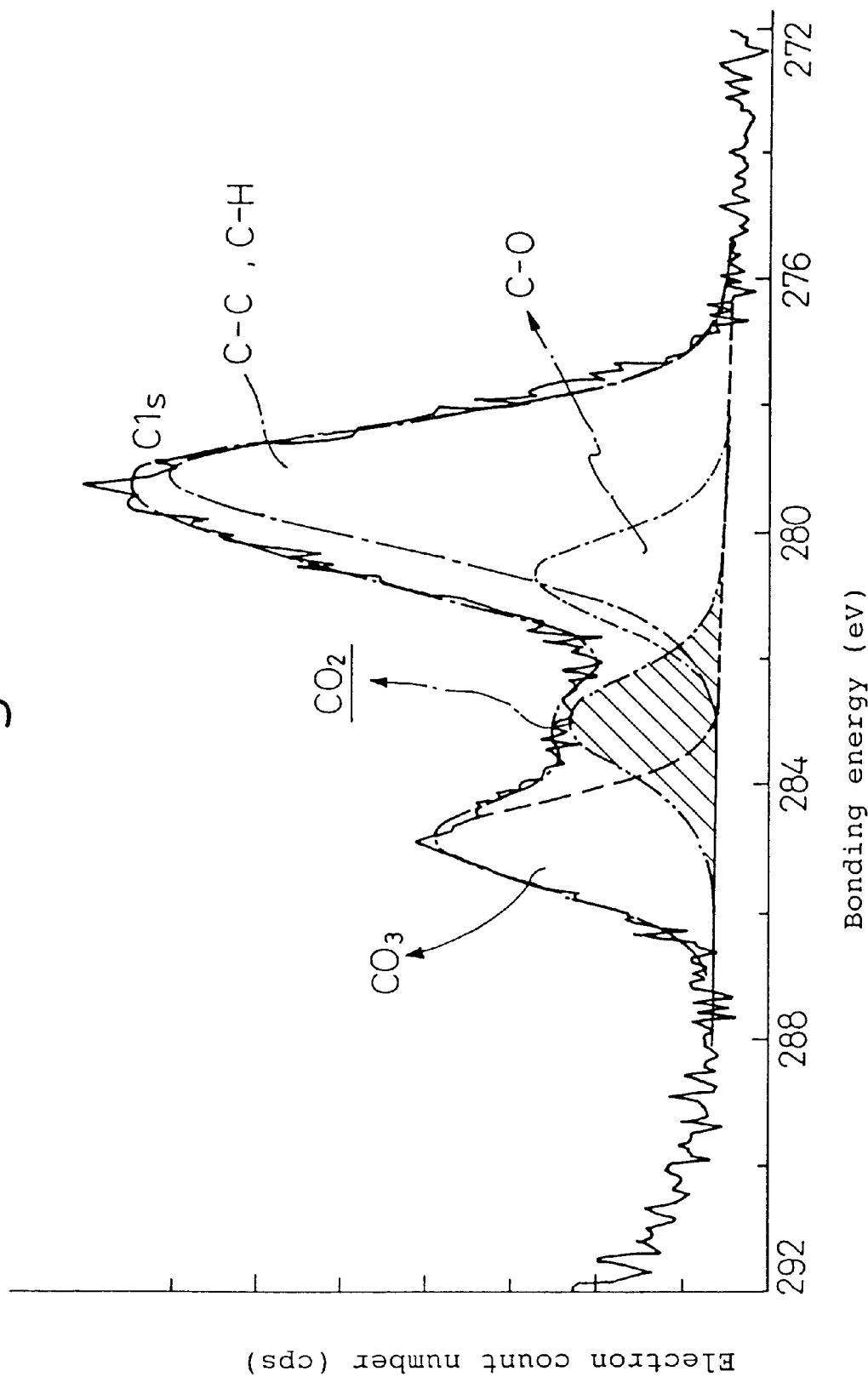
FIG. 15 is an XPS analysis spectral diagram obtained after $CO_2$ was adsorbed to a porous $Tb_2O_3$ test piece.

In order to investigate whether or not the test piece had adsorbed $CO_2$ gas, the test piece was analyzed with the XPS. As a result of the test, it was found that 4 conditions [$CO_3$, $CO_2$, CO, (C—C, C—H)] existed in the C-1s spectrum shown in FIG. 15. Therefore, it was confirmed that $CO_2$ gas existed.

As a test to put this test piece into practical use, the test piece was left for 1 month in a desiccator into which $CO_2$ gas was introduced at a concentration of 10 ppm. While the test piece was left, it was taken out from the desiccator every 10 days and subjected to quantitative analysis using XPS.

Figure 16:
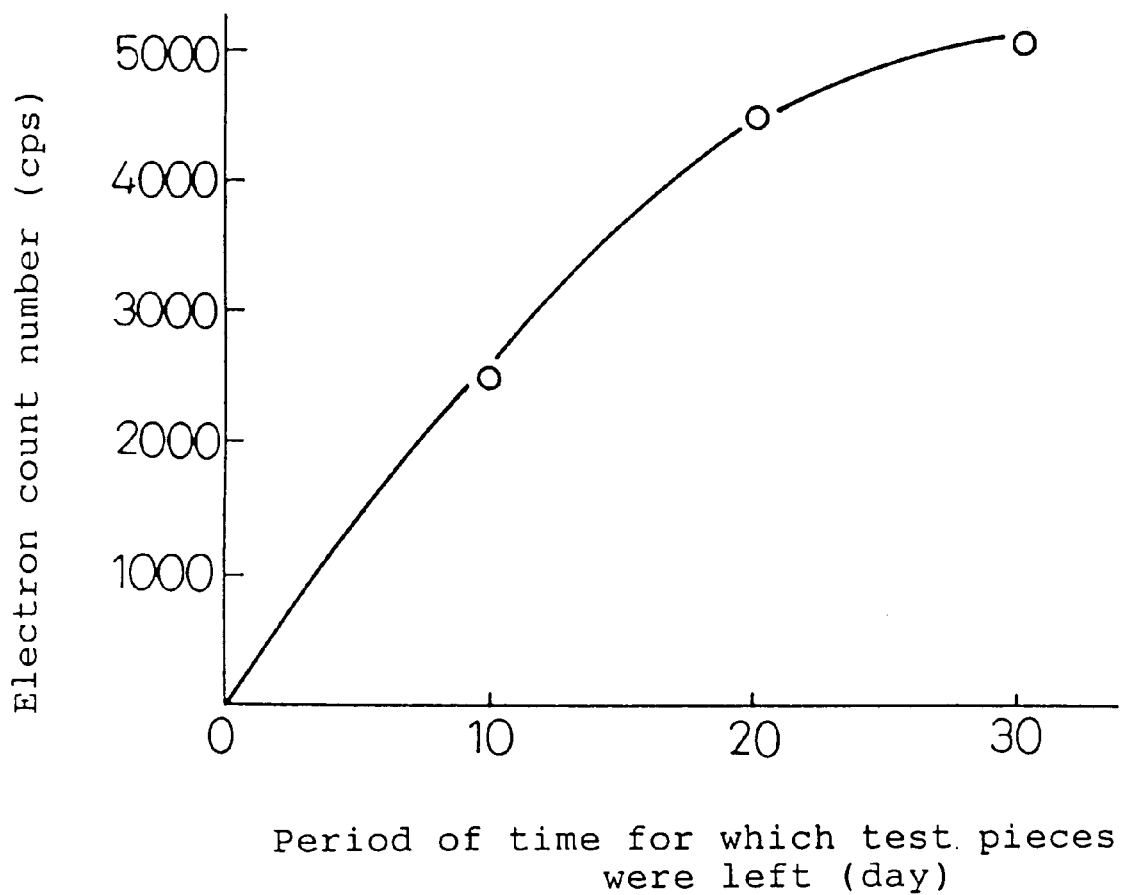
FIG. 16 is a diagram showing a relation between a period of time in which a porous $Tb_2O_3$ test piece was left in $CO_2$ atmosphere, and $CO_2$ intensity.

The experiment was continued. As a result, as shown in FIG. 16, the amount of $CO_2$ increased with the lapse of time, so that a sufficient amount of $CO_2$ for analysis was trapped.

Figure 17:
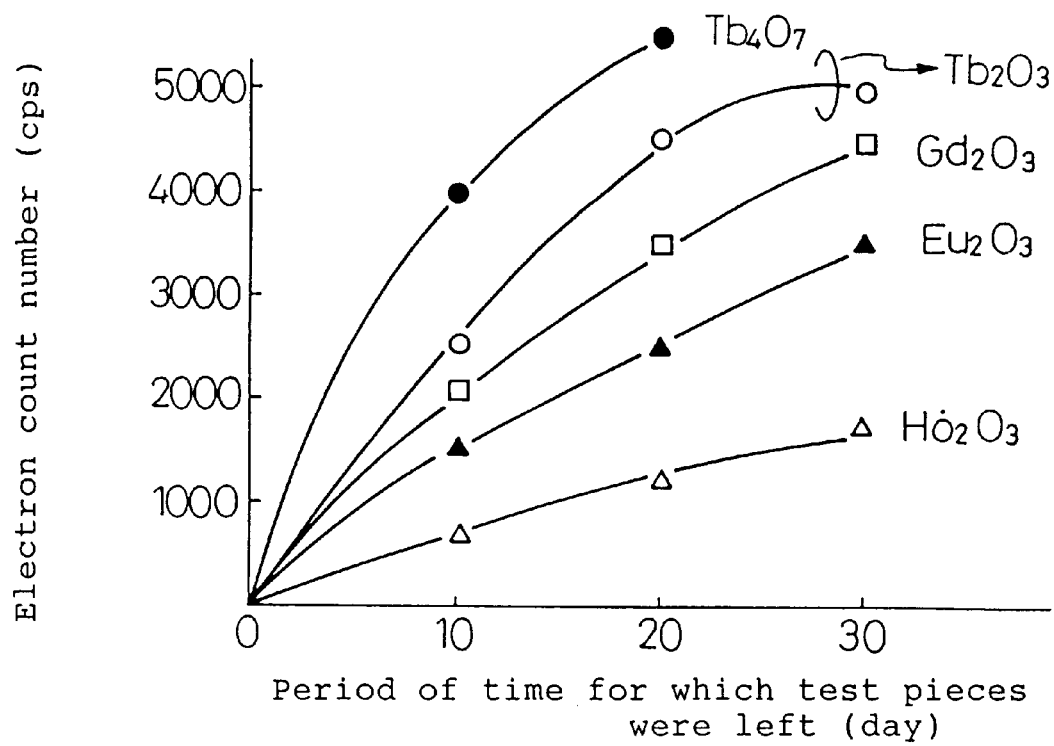
FIG. 17 is a diagram showing a relation between an adsorption amount of $CO_2$ in the case where various types of rare earth metal oxides were used, and a period of time in which the test piece was left.

The same investigation was made using $Eu_2O_3$, $Gd_2O_3$, $Tb_2O_3$, $Tb_4O_7$, $Dy_2O_3$ and $Ho_2O_3$. As a result, as shown in FIG. 17, the same adsorption result as that of the case in which $Tb_2O_3$ was used was provided.

Example 9

As described above, it was found that specific chlorides, for example, CuCl and AgCl were effective as collecting material (a test piece) for selectively collecting $SO_2$. Since the test piece must be handled by a number of operators at various places, the durability and the adherence between a compound and a base material are required. Therefore, metal was selected for the base material. Next, the test piece manufacturing method was investigated so that the adherence between the metal and a compound could be improved. The various investigated methods are shown as follows.

(1) A powder-like compound is pressed into a piece and adhered onto a surface of metal with adhesive.

(2) A powder-like compound and powder-like metal are mixed and pressed into a piece.

(3) The compound is generated on a metal surface in the form of corroded substance.

The following results were provided:

In the case of the test piece made by the method (1), compound tends to collapse and return to the original condition. In the case of the test piece made by the method (2), compound is embedded in the metal, and the surface of the test piece is covered with metallic oxide, which prevents compound from becoming sulfate. For this reason, it was found that the methods (1) and (2) are not effective. On the other hand, it was found that the following method based on (3) is effective.

It has been known that metal corrodes in a chloride gas atmosphere. The inventors found that: in a chloride gas atmosphere, especially in a dry condition (the humidity is not more than 10% RH), only CuCl is formed on the surface of copper, and only AgCl is formed on the surface of silver. Utilizing this corrosive reaction, the inventors made a test piece using the following process.

(1) An apparatus for diluting gas stably and a container for equalizing the diluted gas are prepared, and an atmosphere of dry chloride gas, the concentration of which is 10 ppm, is made.

(2) Oxide and a rust preventive agent on the surfaces of copper and silver sheets (40×5×0.3 mm) are removed by grinding with a grinding wheel, and in order to remove the polished powder, the sheets are subjected to ultrasonic cleaning in which alcohol or acetone is used.

(3) These copper and silver sheets are left in the atmosphere made in the process (1).

(4) After left for 40 hours, the silver and copper sheets, on the surface of which AgCl and CuCl are formed are taken out.

(5) The silver and copper sheets taken out are accommodated in the case shown in FIG. 3A. In order to prevent the degeneration of AgCl and CuCl on the surface, the Ag and Cu sheets are stored in a dry nitrogen atmosphere until the sheets are left in an actual environment.

Using the test piece (measuring kit) made in the aforementioned manner, it was made certain that $SO_2$ gas could be substantially collected. Therefore, 15 types of atmospheres were made, in which the humidity was set at 10, 30, 50, 70 and 90% RH, and $SO_2$ concentration was set at 1 ppm, 100 ppb and 10 ppb. The test pieces were left in the above atmospheres for one month. After that, the test pieces were checked by the following method.

(1) Confirmation by the X-ray microanalyzer (XMA)

Using the XMA, each element can be subjected to qualitative and quantitative analyses. In the case where the metal surfaces of the collection kit left in the $SO_2$ gas environment were changed to $Ag_2SO_3$, $Ag_2SO_4$ and $CuSO_4$, oxygen (O) and sulfur (S) must be detected. Therefore, qualitative analysis was made. According to the analysis, the following results were provided in any humidity condition.

| Results of Qualitative Analysis Made by XMA | | | | | | |
|---|---|---|---|---|---|---|
| Compound on Test Piece | 1 ppm | | 100 ppb | | 10 ppb | |
| | o | S | o | S | o | S |
| AgCl | o | o | o | o | o | o |
| CuCl | o | o | o | o | o | o |

(Remark) o: Existence was confirmed.

After that, an atmosphere of $H_2S$ or an atmosphere of $NO_2$, the concentration and humidity of which were the same as those of the atmosphere of $SO_2$, were made, and the same confirmation tests were carried out. The result was as follows: only when the humidity was 70 and 90% RH, O was confirmed in the test piece, the compound of which was CuCl. The above result was obtained because the standard formation energy of CuCl and that of CuO were approximately the same, and metal was oxidized due to the water contained in the humid atmosphere. Therefore, the principle of collection agrees with the substantial experimental result, so that the appropriateness of the present invention was proved.

(2) Confirmation by X-ray diffraction (XD)

According to the X-ray diffraction, the product on the metal surface can be identified. Accordingly, it was confirmed that $Ag_2SO_3$, $Ag_2SO_4$ and $CUSO_4$ were substantially produced on the metal surface of the test piece left in the gas environment. As a result, the existence of a product similar to sulfate shown here was confirmed in 2 types of test pieces in any environment.

(3) Making a calibration curve

In the qualitative analysis conducted by the XMA, amounts of S atoms were investigated with respect to the test pieces left under these 15 conditions.

As a result, whereas it was found that the amounts of S atoms of CuCl and AgCl samples were constant, a relation between the concentration of $SO_2$ and the amount of S atoms was made clear. Therefore, the calibration curve could be made.

Figure 18:
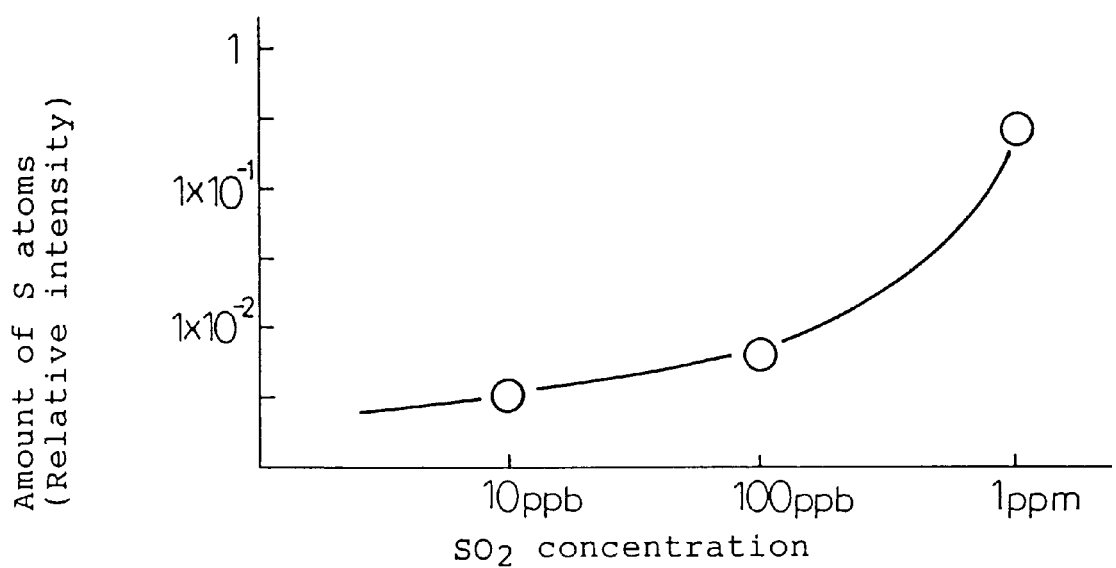
FIG. 18 is a diagram showing an analytical curve of $SO_2$ measurement conducted by silver chloride.

A calibration curve, for a test piece of which is made of AgCl, is shown in FIG. 18.

The test piece was measured by both the conventional method (JIS K-0103) and the method of the present invention in which the test piece was left and the $SO_2$ gas concentration was measured, and the obtained results were compared. The following tables show the results of the test.

| Measured Area "A" (Industrial Area) | |
|---|---|
| | $SO_2$ concentration (ppb) |
| Conventional Method | 83 |
| Present Invention | 80 |

| Measured Area "B" (Residential Area) | |
|---|---|
| | $SO_2$ concentration (ppb) |
| Conventional Method | 26 |
| Present Invention | 30 |

| Measured Area "C" (Overseas) | |
|---|---|
| | $SO_2$ concentration (ppb) |
| Conventional Method | 46 |
| Present Invention | 50 |

In the case of test pieces of CuCl, the same result was provided.

As a result of the experiments, it was confirmed that the same values as those of the conventional test pieces were provided by these test pieces.

As can be seen from the examples described above, $SO_2$ could be collected by these test pieces. After the test pieces had been left in an environment, the gas concentration of which was changed, the test pieces were subjected to quantitative analysis, and the calibration curve was made. Therefore, these test pieces can be applied to actual measurements.

Example 10

For the purpose of investigating the effect of an umbrella to which the test piece 13 for measuring the environmental gas (when the test piece is set in a case, it is referred to as a test piece kit) was applied as a simple type environment measuring sample wherein the test piece 13 for measuring the environmental gas was set in the protective case 10 shown in FIG. 3A, an environmental investigation was made outside an ordinary house located in a city area. In this experiment, Cu, Ag, Al, Fe and Fe—Ni were used for the test pieces. Three test piece kits were prepared, and the first set of them was hung from the inside of a large eave with a cord inserted into the hole 14 formed on the case so that the test piece kits did not get wet with rain. The second set was provided with an umbrella of the invention and hung from a clothes pole in a yard facing the eaves. The third set was hung from the clothes pole as it was. Roofs were not provided above the clothes pole, so that the second and third sets were exposed to the rain.

In this connection, the hole 14 of the umbrella may be sealed with clay and other materials if necessary.

Figures 19A, 19B, 19C:
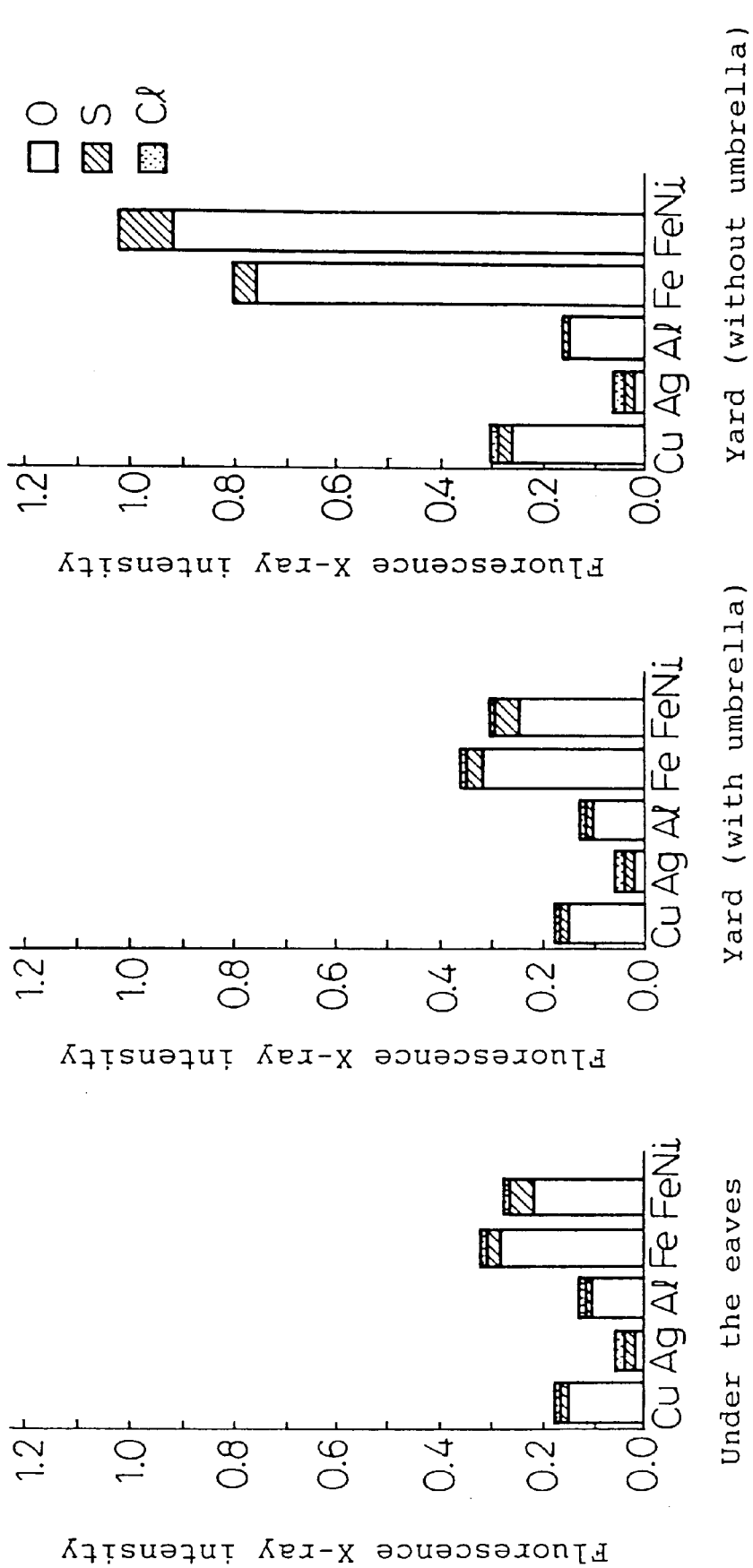
FIGS. 19A to 19C are diagrams showing the results of analysis of corrosion products produced on test pieces in the case where the measuring kits were placed under the eaves, in the yard (with an umbrella), and in the yard (without an umbrella).

These test piece kits were left for one month. While the test piece kits were left, it rained several times. After a predetermined period of time had passed, the X-ray intensities of oxygen O, sulfur S and chloride Cl in the corrosive product formed on each test piece were measured with the fluorescence X-ray analyzer. The results of the experiment are shown in FIGS. 19A, 19B, and 19C. In the case of the sample without a roof and an umbrella, since the air entrance 15 of the case was provided upward, the rain water entered the case from the air entrance 15, and came into contact with the sample. Accordingly, as shown in FIGS. 19A to 19C, the samples were remarkably corroded by the rain water, which is a corrosion factor except for gas, as compared with the sample hung from the eaves. Further, since Cl was deposited together with the rain water, accurate values were not provided. However, an amount of corrosion of the sample hung from the eaves and that of the sample provided with the umbrella were approximately the same. That is, it was confirmed that the sample did not get wet with the rain because of the umbrella, and a sufficient amount of air was supplied to the sample, so that the gas measurement was accurately performed.

Example 12

In order to confirm the effects of the apparatus shown in FIGS. 5A and 5B, two types of apparatus were prepared. One was an apparatus provided with a dry battery so as to investigate a relation between the wind speed above the test piece and the reactivity of the gas and test piece, and the wind speed above the test piece was set to be each of 0.1, 0.2, 0.3, 0.4, 0.5, 0.6, 0.7, 0.8, 0.9 and 1.0 m/s. The other was an apparatus not provided with a dry battery. In this case, test pieces of silver Ag were prepared, as silver Ag remarkably reacts with hydrogen sulfide $H_2S$, and S compounds are generated on the surface. The test pieces of silver Ag were accommodated in the cases, wherein 11 sets of test pieces were prepared so as to be assembled to each apparatus. $H_2S$ gas was introduced into each set by the concentration of 10 ppm. Each set was left for 2 weeks in a desiccator, the temperature of which was 20° C. and the humidity of which was 80%. After that, each test piece was analyzed. The fluorescence X-ray analyzer was used for the analysis, and the X-ray intensity of S contained in the compound produced on the Ag surface was measured.

Figure 20:
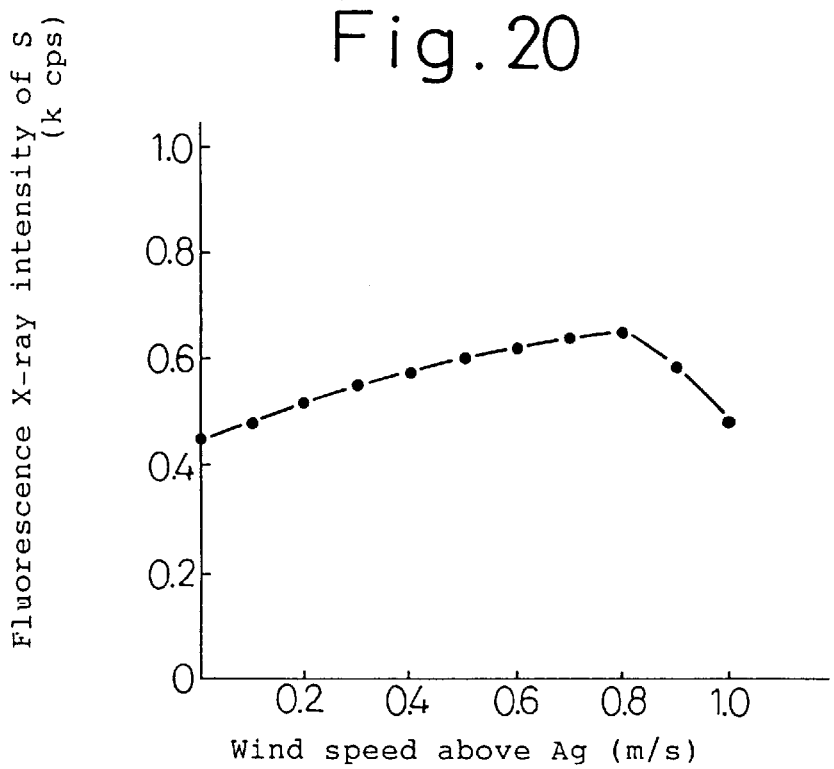
FIG. 20 is a diagram showing an amount of sulfur (S) reacted with a silver test piece in the case where air was sent to the silver test piece at a predetermined speed.

The results are shown in FIG. 20.

Since the X-ray intensity represents an amount of S, the following was proved by FIG. 20:

In the case where gas was supplied at a certain speed and came into contact with the surface of a test piece, an amount of reaction caused between the gas and the test piece was increased as compared with a case in which the test piece was left as it was. Further, a reaction caused between Ag and $H_2S$ was most facilitated at a certain wind speed, and the wind speed was 0.8 m/s.

Next, two sets of Ag test pieces provided in a case were prepared. One of them was left being not assembled to an apparatus, and the other was assembled to an apparatus in which the wind speed of the upper portion of the test piece was set to be 0.8 m/s. Under the aforementioned condition, the test pieces were left in a desiccator into which $H_2S$ gas was introduced by the concentration of 10 ppm, and the temperature in the desiccator was maintained at 20° C. and the humidity was maintained at 80%. The test pieces were taken out from the desiccator at various times and the X-ray intensity of S was measured.

Figure 21:
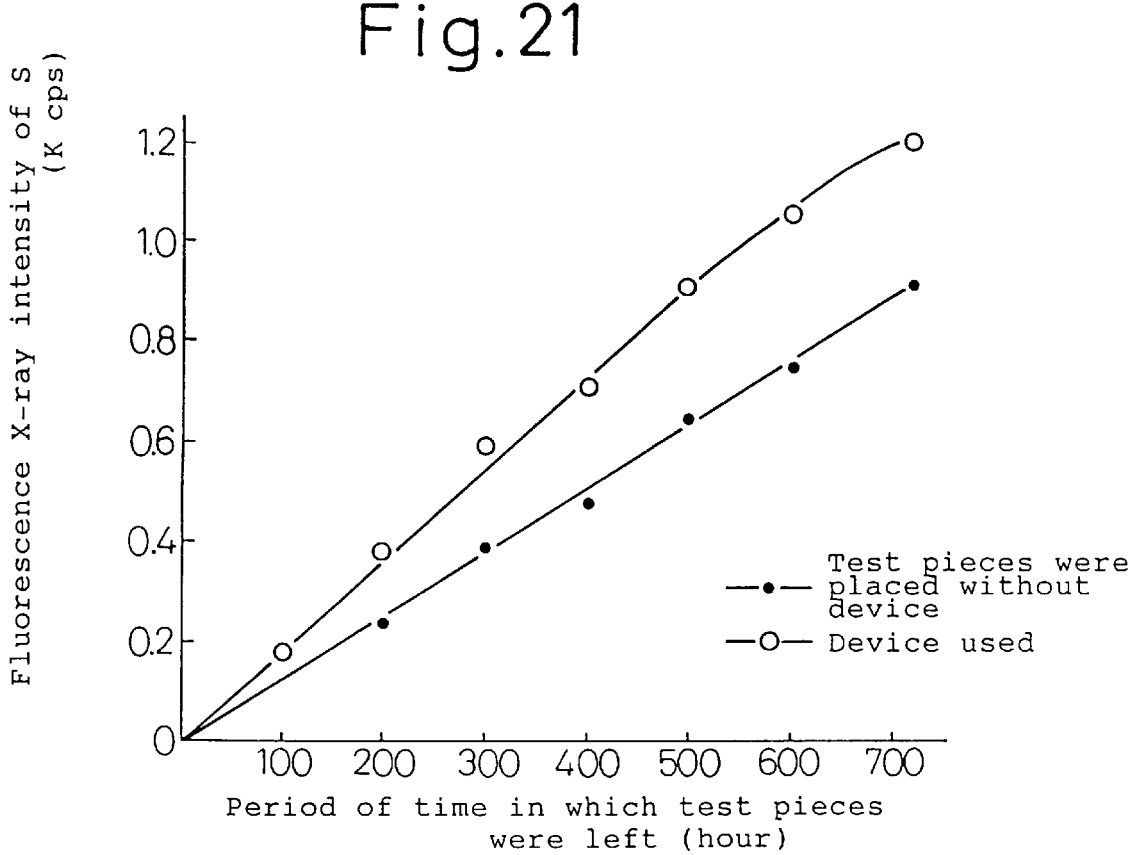
FIGS. 21 and 22 are diagrams showing a relation between a period of time in which a test piece was left, and an amount of sulfur reacted with the test piece in the case where the acceleration devices shown in FIGS. 5A, 5B and FIGS. 6A, 6B were used.

The result of the experiment is shown in FIG. 21. As shown in the drawing, in three weeks, the amount of reaction caused between Ag and S in the case assembled to the apparatus reached an amount of reaction caused between Ag and S for one month in the case not assembled to the apparatus. Consequently, it was confirmed that this apparatus has the effect of facilitating the reaction caused between the gas and test piece.

Example 13

In order to make certain of the effect of the apparatus shown in FIGS. 6A and 6B, in the same manner as that of Example 11, two sets of Ag test pieces provided in a case were prepared. One of them was left being not assembled to an apparatus, and the other was assembled to an apparatus in which the wind speed of the upper portion of the test piece was adjusted to be 0.8 m/s by the variable resistor 39 in accordance with the result shown in FIG. 20. Under the aforementioned condition, the test pieces were left in a desiccator into which $H_2S$ gas was introduced by the concentration of 10 ppm, and the temperature in the desiccator was maintained at 20° C. and the humidity was maintained at 80%. The test pieces were taken out from the desiccator at various times and X-ray intensity of S was measured.

Figure 22:
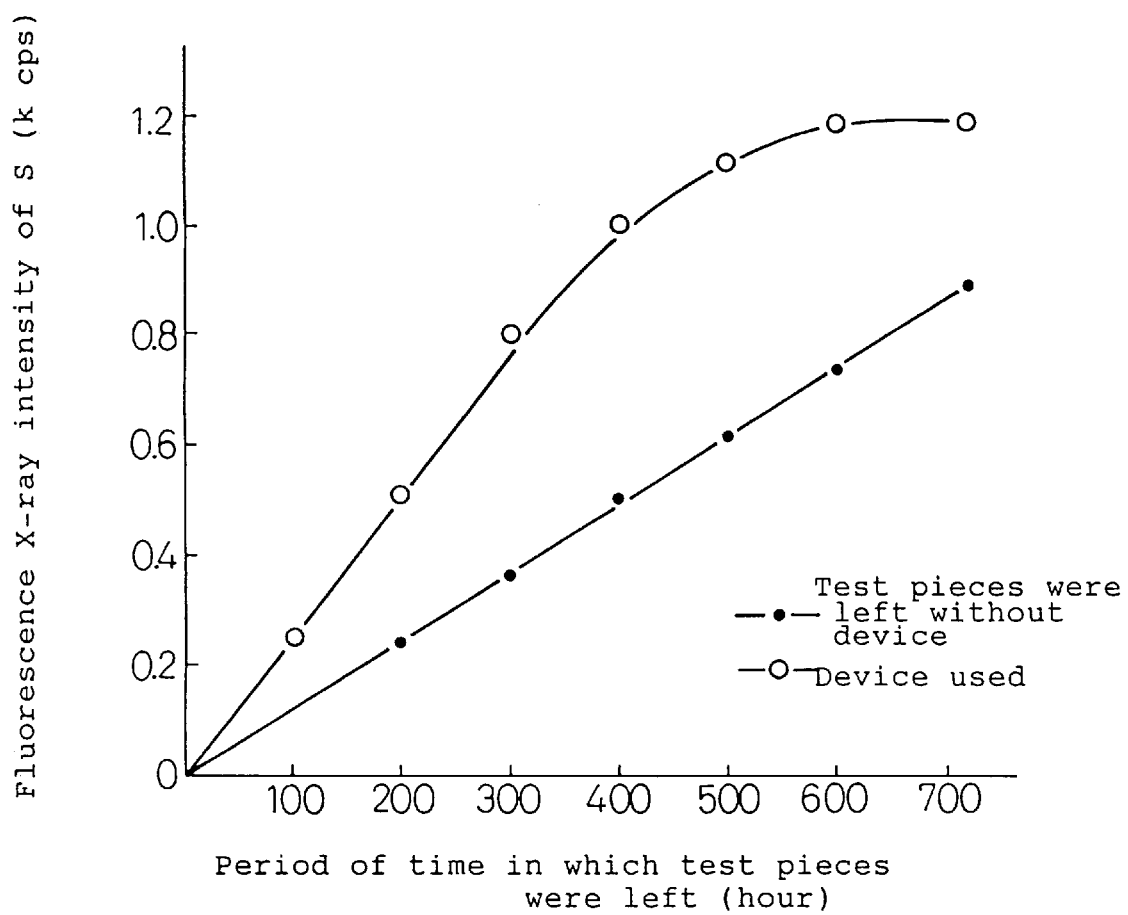

The result of the experiment is shown in FIG. 22.

As shown in the drawing, in two weeks, an amount of reaction caused between Ag and S in the case assembled to the apparatus reached an amount of reaction caused between Ag and S for one month in the case not assembled to the apparatus. Consequently, it was confirmed that this apparatus has the effect of facilitating the reaction caused between the gas and test piece.

In Example 12, the construction of Example 11 was improved since it was disadvantageous in that gas was trapped by the inner walls and the fan as the air entrance is distant from the case. As a result of the improvement, the reaction was effectively facilitated.

Example 14

The effect of the apparatus shown in FIGS. 7A, 7B and 7C was determined in the following manner. One set of apparatus provided with the dry battery 32 was prepared, so that the wind speed in the upper position of the test piece was adjusted to be 0.15, 0.25, 0.45, 0.65, 1.00 and 1.30 m/s, and two sets of apparatus not provided with the dry battery 32 were prepared. In this connection, one of the apparatus is referred to as (1), and the other is referred to as (2). Test pieces of copper Cu and silver Ag were prepared, which remarkably react with hydrogen sulfide so that compounds of sulfur S are produced on the surface. Then, a set of test pieces Cu and Ag were accommodated in a case. Then, 8 sets of test pieces, each set including Cu and Ag test pieces, were prepared and respectively assembled to the apparatus. The sets of test pieces except for (2) were left for 2 weeks in a desiccator into which $H_2S$ gas was introduced at a concentration of 100 ppb, and the temperature in the desiccator was maintained at 25° C. and the humidity was maintained at 60%. The sets of test pieces in (2) were left in the desiccator for one month. After that, each test piece was analyzed. For the analysis, the fluorescence X-ray analyzer was used, and the X-ray intensity of S contained in the compounds produced on the surfaces of Cu and Ag was measured.

Figure 23:
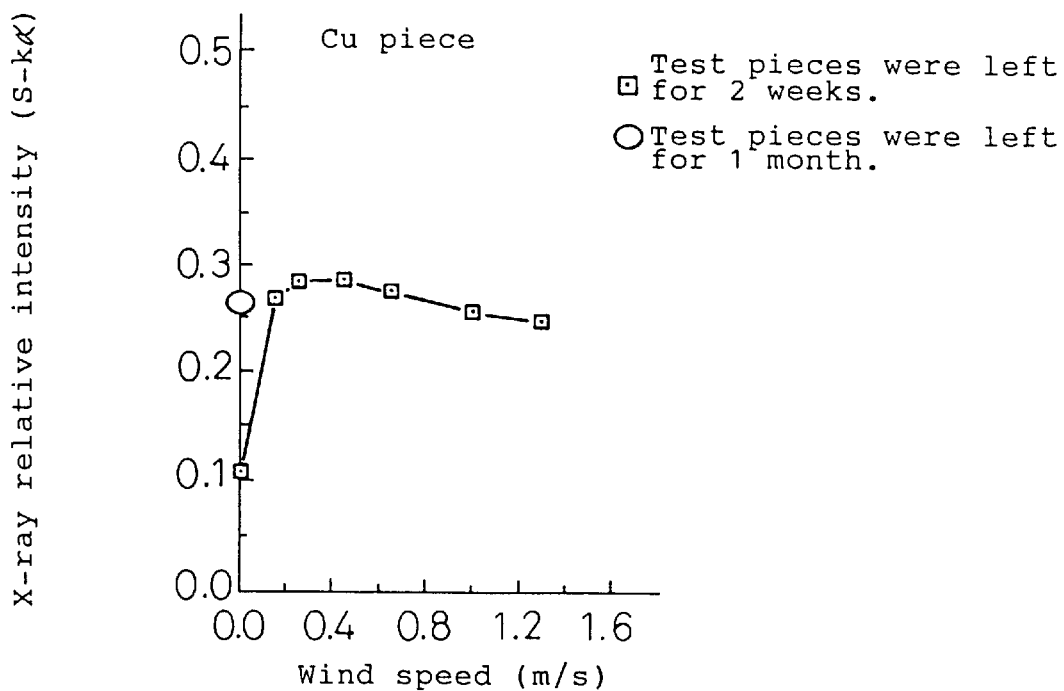
FIGS. 23 and 24 are diagrams showing the variation of an amount of sulfur (S) reacted with a test piece in the case where the wind speed was changed in the acceleration device shown in FIGS. 7A to 7C.
Figure 24:
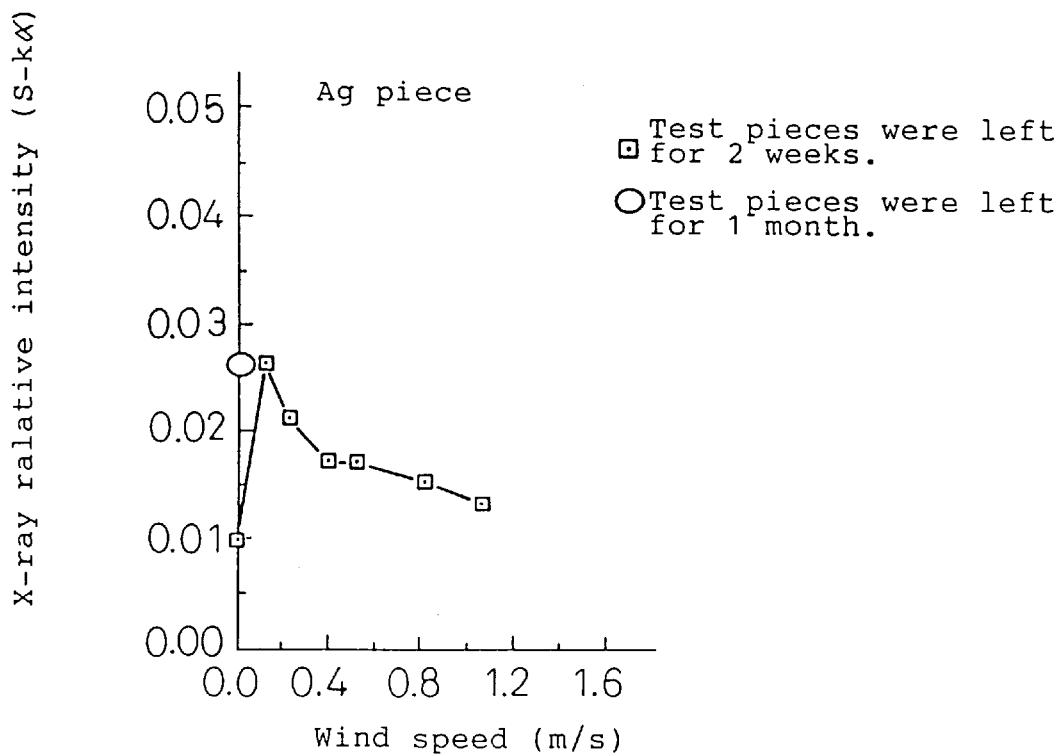
Figure 26:
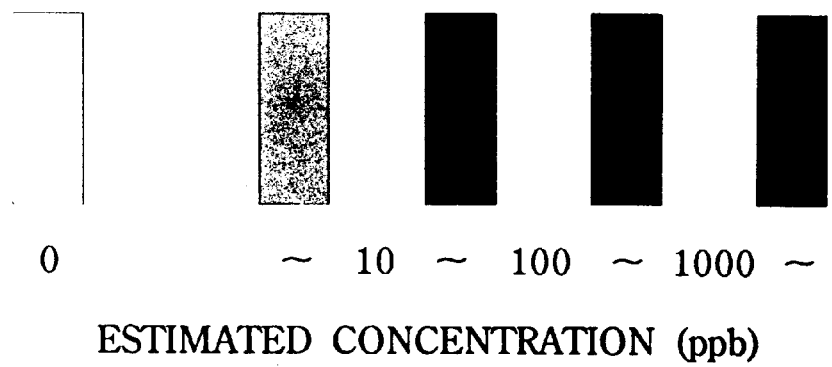
FIGS. 26 to 29 are color photographs of a series of color or appearance samples.
Figure 27:
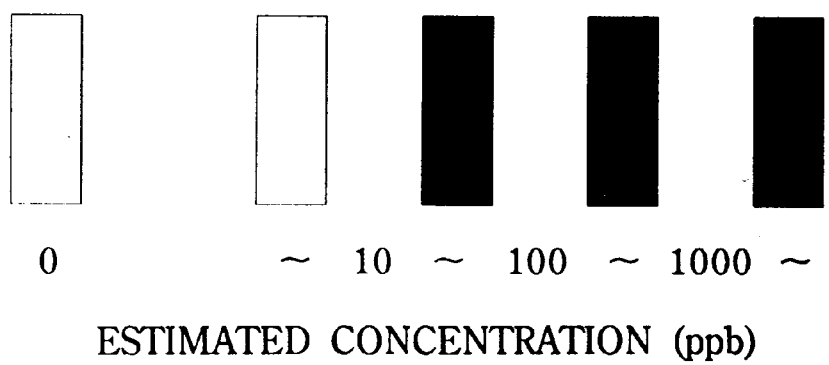
Figure 28:
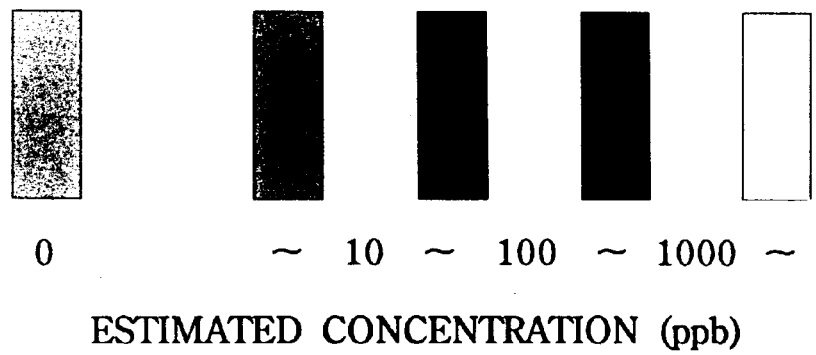
Figure 29:
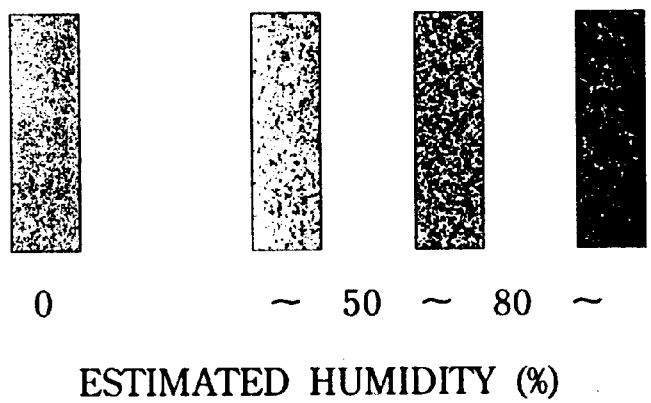
Figure 30:
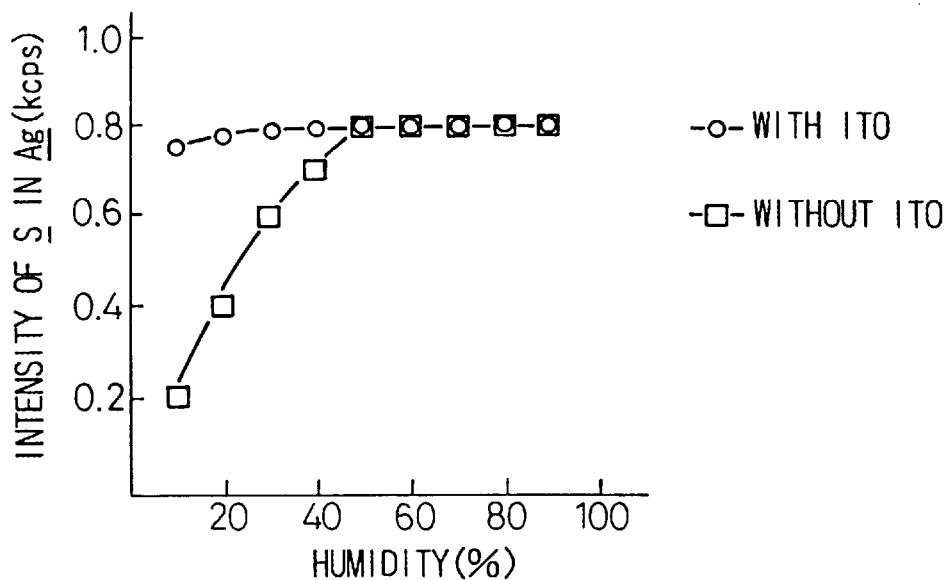
FIG. 30 shows the amount of sulfur in a silver test piece placed in an environment with a certain humidity.
Figure 31:
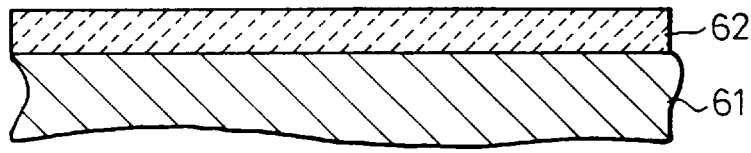
FIG. 31 is a cross-sectional view of a test piece having a coating of indium oxide and/or tin oxide.
Figure 32:
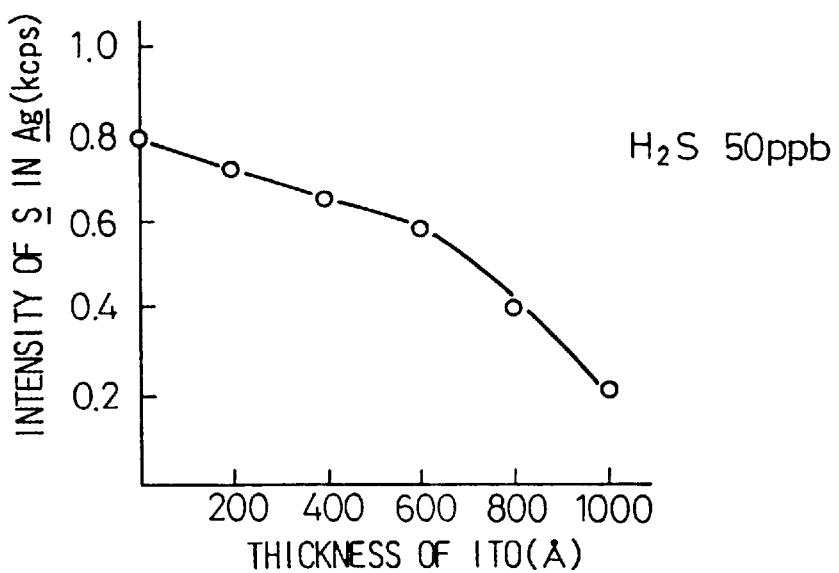
FIGS. 32 and 33 show the effect of the ITO coating on the amount of sulfur in a silver test piece placed in a dry environment.
Figure 33:
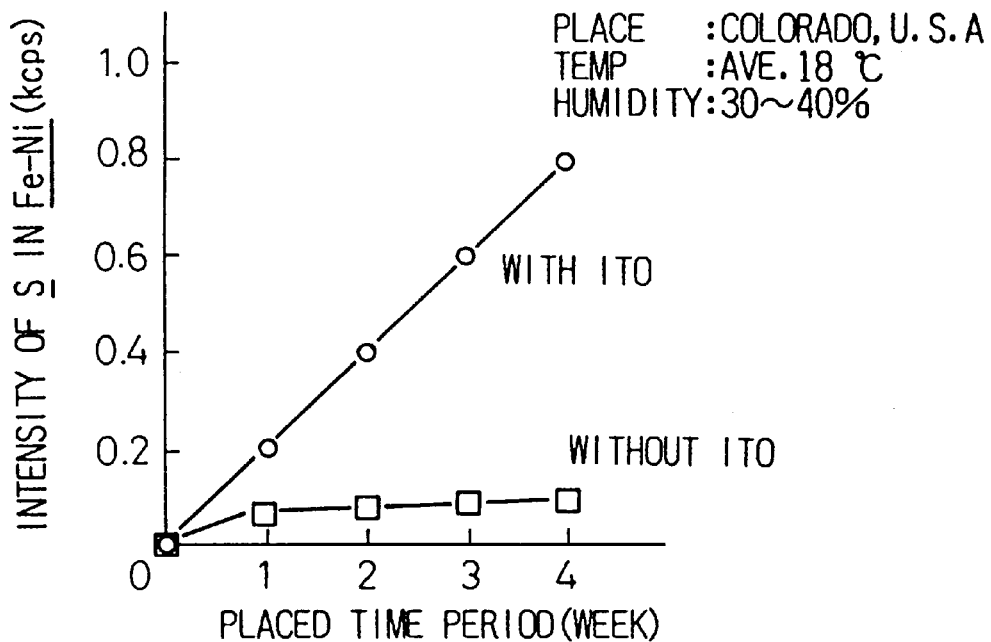
Figure 34:
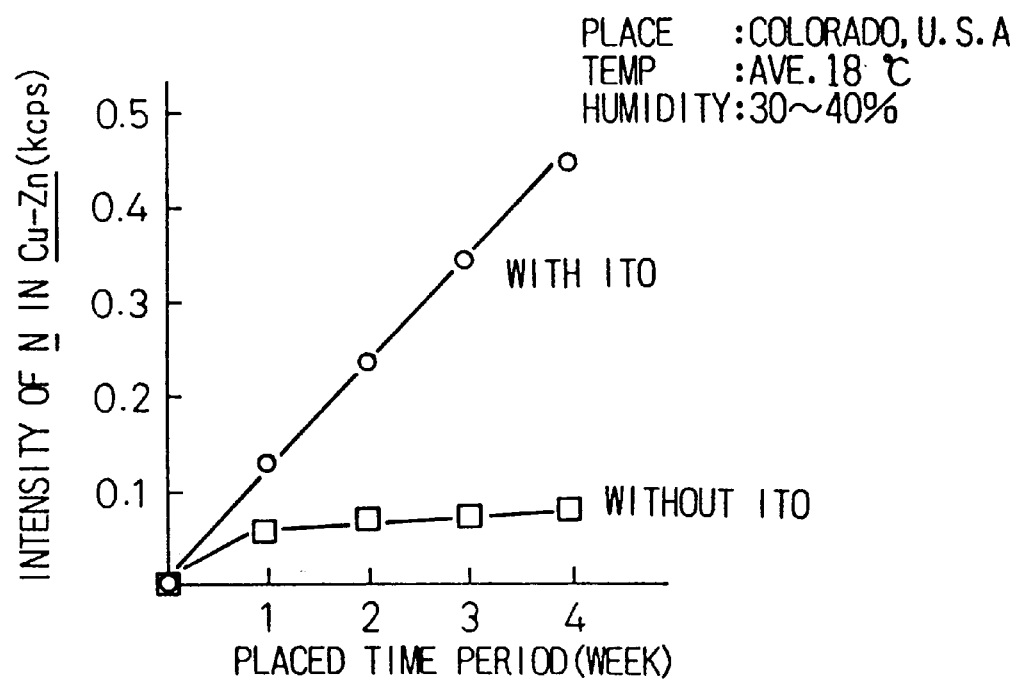
FIG. 34 shows the effect of the ITO coating on the amount of nitrogen in a brass test piece placed in a dry environment.

The results are shown in FIGS. 23 and 24. The X-ray intensity represents the amount of S. As can be seen from FIGS. 23 and 24, when a wind was blown against the test pieces by this apparatus at a speed of 0.15 m/s for 2 weeks, the same corrosion amount as that of the test pieces left for one month in the conventional manner was provided.

The apparatus of Example 13 is characterized in that: the dry batteries are connected in parallel in order to reduce the consumption of the dry batteries; and consideration is given to the layout of parts in the apparatus, and the size and weight of the apparatus are reduced so that the dry batteries can be easily attached to and detached from the apparatus. Also, when the reduced period in which the test piece is left is determined to be 2 weeks, and the wind speed is determined to be 0.15 m/sec, the same corrosion amount as that of the test piece that has been left for one month can be provided. Therefore, the operational data of the apparatus of the present invention corresponds to the data accumulated in the past, so that the conventional data can be effectively utilized.

[Industrially Applicable Possibility]

The apparatus of the present invention can be made compact and produced at low cost. Further, the apparatus is capable of simply monitoring an average concentration of specific gas (especially, $NO_x$, $CO_2$, and $SO_2$ gas) in an environment over a long period of time at an arbitrary location. Accordingly, the apparatus of the present invention can be applied to the measurement of environmental pollution which has recently become a problem to be solved and, further, can be applied to the evaluation of an environment in which precision machines and electronic equipment are installed.

We claim:

1. A kit for collecting an environmental sample from an environmental atmosphere for use in determining, from the collected environmental sample, respective concentrations of $NO_x$, $CO_2$ or $SO_2$ in the environmental atmosphere, the kit comprising:

a test piece made of a metal, a ceramic or a metallic salt material, having an exposed surface and a porous structure in at least a layer including the exposed surface and selectively adsorbing $NO_x$, $CO_2$ or $SO_2$ gas in the environmental atmosphere; and a case disposing the test piece in the environmental atmosphere to collect the environmental sample.

2. The kit according to claim 1 wherein, for use in determining the concentration of $CO_2$ contained in the environmental atmosphere, said test piece is made of a porous metallic oxide material selected from $La_2O_3$, $Ce_2O_3$, $Pr_2O_3$, $Nd_2O_3$, $Pm_2O_3$, $Sm_2O_3$, $Eu2O_3$, $Gd_2O_3$, $Tb_2O_3$, $Tb_3O_7$, $Dy_2O_3$, $Ho_2O_3$, $Er_2O_3$, $Tm_2O_3$, and $Yb_2O_3$ materials.

3. The kit according to claim 1 wherein, for use in determining the concentrations of at least two of $NO_x$, $CO_2$ and $SO_2$, said kit includes not less than 2 of said test pieces.

4. The kit according to claim 1, wherein the test piece collects an environmental gas sample of one of $NO_x$, $CO_2$ or $SO_2$ environmental gases in an amount or at a rate, over a selected time duration and in relation to the concentration of the environmental gas in the environmental atmosphere, so that the test piece on which the gas is collected can be used to determine the average concentration of the collected gas in the environmental atmosphere over the selected time duration.

5. The kit according to claim 1, wherein the density of a porous ceramic structure is not more than 2 grams per $cm^3$.

6. The kit according to claim 1, wherein the test piece is made of a brass-based metal having an internal stress of at least approximately 100 MPa.

7. The kit according to claim 1, wherein the porous structure of a surrounding material comprises fine ceramic powder having a particle size of from 0.05 μm to 5 μm.

8. The kit according to claim 1, wherein the $NO_x$, $CO_2$ or $SO_2$ gas is absorbed on the exposed surface of the metal or the ceramic material and reacts with but is not absorbed by the copper chloride or silver chloride material.

9. The kit according to claim 1 wherein, for use in determining the concentration of $SO_2$ contained in the environmental atmosphere, said test piece is made of a metal chloride material which has a free formation energy of chloride larger which is than a free formation energy of sulfate.

10. The kit according to claim 9, wherein said metallic chloride material is a selected one of copper chloride and silver chloride materials.

11. The kit according to claim 9, wherein the $NO_x$, $CO_2$ or $SO_2$ gas is absorbed on the exposed surface of the metal or the ceramic material and reacts with but is not absorbed by the copper chloride or silver chloride material.

12. The kit according to claim 1, wherein the porous structure comprises sintered metallic particles or ceramic powder.

13. The kit according to claim 12, wherein the density of a porous structure is not more than 7 grams per $cm^3$.

14. The kit according to claim 1, wherein said test piece is made of a porous metal material or a porous ceramic material on which a layer of fine metallic particles or a layer of ceramic powder, respectively, is carried, or of a solid metal material or a solid ceramic material on which a layer of fine metallic particles or a layer of ceramic powder, respectively, is carried.

15. The kit according to claim 14 wherein, for use in determining the concentration of $NO_x$ in the environmental atmosphere, said porous ceramic material or said layer of particulate ceramic is a selected one of $SiO_2$-$Al_2O_3$, $YBa_2Cu_3O_x$, $CrO_2$, $Cr_2O_3$, $Fe_2O_3$, $Co_2O_3$, $SnO_2$, $CoAl_2O_4$, CuO, $Al_2O_3$, and MgO materials.

16. The kit according to claim 14 wherein, for use in determining the concentration of $NO_x$ contained in the environmental atmosphere, said test piece is made of a porous metal material or a porous ceramic material, each having voids therein filled with triethanolamine.

17. The kit according to claim 14, wherein the test pieces have metallic particle sizes in the range from 30 μm to 200 μm.

18. The kit according to claim 14 wherein, for use in determining the concentration of $NO_x$ in the environmental atmosphere, said porous metal material or said layer of fine metallic particles is a selected one of copper, silver, platinum, rhodium, ruthenium, palladium, iridium and nickel materials.

19. The kit according to claim 18, wherein the selected metal material is copper.

20. A kit for collecting an environmental sample from an environmental atmosphere for use in determining, from the collected environmental sample, a concentration of at least one of $NO_x$, $CO_2$ and $SO_2$ contained in the environmental atmosphere, the kit comprising:

a test piece made of a metal, a ceramic or a metallic salt material having an exposed surface and a porous structure in at least a layer including the exposed surface and selectively adsorbing $NO_x$, $CO_2$ or $SO_2$ gas in the environmental atmosphere, the test piece being made of at least one of:

i) porous metal or porous ceramic, or solid metal or solid ceramic on a surface of which a layer of fine metallic particles or a layer of ceramic powder, respectively, are carried, the metal of the porous metal or of the fine metallic particles layer being selected from the group consisting of copper, silver, platinum, rhodium, ruthenium, iridium and nickel, the ceramic of the porous ceramic or of the ceramic powder layer being selected from the group consisting of $SiO_2$—$Al_2O_3$, $YBa_2Cu_3O_x$, $CrO_2$, $Cr_2O_3$, $Fe_2O_3$, $Co_2O_3$, $SnO_2$, $CoAl_2O_3$, $CuO$, $Al_2O_3$ and $MgO$;

ii) a porous metal or a porous ceramic, each having voids therein which are filled with triethanolamine, for collecting a sample for use in determining the concentration of $NO_x$;

iii) a porous oxide of a rare earth metal selected from the group consisting of $La_2O_3$, $Ce_2O_3$, $Pr_2O_3$, $Nd_2O_3$, $Pm_2O_3$, $Sm_2O_3$, $Eu_2O_3$, $Gd_2O_3$, $Tb_2O_3$, $Tb_3O_7$, $Dy_2O_3$, $Ho_2O_3$, $Er_2O_3$, $Tm_2O_3$ and $Yb_2O_3$ for collecting a sample for use in determining the concentration of $CO_2$; and iv) copper chloride or silver chloride for collecting a sample for use in determining the concentration of $SO_2$.

21. The kit according to claim 20 wherein, for use in determining the concentrations of at least two of $NO_x$, $CO_2$ and $SO_2$, said kit includes not less than 2 of said test pieces.

22. The kit according to claim 20, wherein the test piece collects an environmental gas sample of one of $NO_x$, $CO_2$ or $SO_2$ environmental gases in an amount or at a rate, over a selected time duration and in relation to the concentration of the environmental gas in the environmental atmosphere, so that the test piece on which the gas is collected can be used to determine the average concentration of the collected gas in the environmental atmosphere over the selected time duration.

23. A kit for collecting an environmental sample from an environmental atmosphere the collected environmental sample affording a basis for determining respective concentrations of $NO_x$, $CO_2$ or $SO_2$ in the environmental atmosphere, the kit comprising:

a test piece made of a metal, a ceramic or a metallic salt material of copper chloride or silver chloride, having an exposed surface and a porous structure in at least a layer including the exposed surface $NO_x$, $CO_2$ or $SO_2$ gas in the environmental atmosphere; and a case disposing the test piece in the environmental atmosphere to collect the environmental sample.

24. The kit according to claim 23, wherein the $NO_x$, $CO_2$ or $SO_2$ gas is absorbed on the exposed surface of the metal or the ceramic material and reacts with but is not absorbed by the copper chloride or silver chloride material.

25. A kit for collecting an environmental sample from an environmental atmosphere the collected environmental sample affording a basis for determining a concentration of at least one of $NO_x$, $CO_2$ and $SO_2$ contained in the environmental atmosphere, the kit comprising:

a test piece made of a metal, a ceramic or a metallic salt material having an exposed surface and a porous structure in at least a layer including the exposed surface, the test piece being made of at least one of:

i) porous metal or porous ceramic, or solid metal or solid ceramic on a surface of which a layer of fine metallic particles or a layer of ceramic powder, respectively, are carried, the metal of the porous metal or of the fine metallic particles layer being selected from the group consisting of copper, silver, platinum, rhodium, ruthenium, iridium and nickel, the ceramic of the porous ceramic or of the ceramic powder layer being selected from the group consisting of $SiO_2$—$Al_2O_3$, $YBa_2Cu_3O_x$, $CrO_2$, $Cr_2O_3$, $Fe_2O_3$, $Co_2O_3$, $SnO_2$, $CoAl_2O_3$, $CuO$, $Al_2O_3$ and $MgO$;

ii) a porous metal or a porous ceramic, each having voids therein which are filled with triethanolamine, for collecting a sample for use in determining the concentration of $NO_x$;

iii) a porous oxide of a rare earth metal selected from the group consisting of $La_2O_3$, $Ce_2O_3$, $Pr_2O_3$, $Nd_2O_3$, $Pm_2O_3$, $Sm_2O_3$, $Eu_2O_3$, $Gd_2O_3$, $Tb_2O_3$, $Tb_3O_7$, $Dy_{2O3}$, $Ho_2O_3$, $Er_2O_3$, $Tm_2O_3$ and $Yb_2O_3$ for collecting a sample for use in determining the concentration of $CO_2$;

iv) copper chloride or silver chloride for collecting a sample for use in determining the concentration of $SO_2$.

26. The kit according to claim 25, wherein the $NO_x$, $CO_2$ or $SO_2$ gas is absorbed on the exposed surface of the metal or the ceramic material and reacts with but is not absorbed by the copper chloride or silver chloride material.

* * * * *